(12) United States Patent  
Shalgi et al.

(10) Patent No.: US 11,864,781 B2  
(45) Date of Patent: Jan. 9, 2024

(54) ROTATING FRAME THROMBECTOMY DEVICE

(71) Applicants: Neuravi Limited, Galway (IE); Biosense Webster (Israel) Ltd., Yokneam (IL)

(72) Inventors: Avi Shalgi, Yokneam Illit (IL); David Vale, Galway (IE)

(73) Assignees: NEURAVI LIMITED, Galway (IE); BIOSENSE WEBSTER (ISRAEL) LTD., Yokneam (IL)

( * ) Notice: Subject to any disclaimer, the term of this patent is extended or adjusted under 35 U.S.C. 154(b) by 315 days.

(21) Appl. No.: 17/030,028

(22) Filed: Sep. 23, 2020

(65) Prior Publication Data

US 2022/0087700 A1 Mar. 24, 2022

(51) Int. Cl.
*A61B 17/221* (2006.01)
*A61B 17/22* (2006.01)
*A61B 17/00* (2006.01)

(52) U.S. Cl.
CPC ...... *A61B 17/22031* (2013.01); *A61B 17/221* (2013.01); *A61B 2017/00367* (2013.01)

(58) Field of Classification Search
CPC .......... A61B 17/221; A61B 2017/2215; A61B 17/22031; A61B 2017/22034; A61F 2/01; A61F 2/0103; A61F 2/0105; A61F 2/011; A61F 2/012; A61F 2/013;

(Continued)

(56) References Cited

U.S. PATENT DOCUMENTS

| 2,828,147 A | 12/1899 | Peiffer |
| 3,361,460 A | 1/1968 | Gerhart et al. |
| 4,455,717 A | 6/1984 | Gray |

(Continued)

FOREIGN PATENT DOCUMENTS

| CN | 2557083 Y | 6/2003 |
| CN | 101172051 A | 5/2008 |

(Continued)

OTHER PUBLICATIONS

US 6,348,062 B1, 02/2002, Hopkins et al. (withdrawn)
Extended European Search Report dated Feb. 17, 2022 issued in corresponding EP Appln. No 21 19 8179.

*Primary Examiner* — Wade Miles
(74) *Attorney, Agent, or Firm* — TROUTMAN PEPPER HAMILTON SANDERS LLP

(57) ABSTRACT

A device for removing a clot from a vessel can have dual layers where an inner expandable body runs within an outer expandable body. The device can have a collapsed delivery configuration, an expanded deployed configuration, and a clot pinching configuration. The inner and outer bodies can be a plurality of cells formed by a network of struts. The openings of the cells align when the device is deployed within the clot, where the radial force from the expanding bodies urges portions of the clot through the openings. The inner and outer bodies can be configured to be selectively translatable relative to each other, so that the portions of the clot in the cell openings can be compressed and gripped when the translation transitions the device to the clot pinching configuration. The translation can be maintained to pinch the clot as it is retrieved from the patient.

15 Claims, 6 Drawing Sheets

(58) Field of Classification Search
CPC ......... A61F 2002/016; A61M 25/0133; A61M 25/0136; A61M 25/0147
See application file for complete search history.

(56) References Cited

U.S. PATENT DOCUMENTS

| | | |
|---|---|---|
| 4,611,594 A | 9/1986 | Grayhack et al. |
| 4,612,931 A | 9/1986 | Dormia |
| 4,643,184 A | 2/1987 | Mobin-Uddin |
| 4,727,873 A | 3/1988 | Mobin-Uddin |
| 4,793,348 A | 12/1988 | Palmaz |
| 4,873,978 A | 10/1989 | Ginsburg |
| 5,011,488 A | 4/1991 | Ginsburg |
| 5,084,065 A | 1/1992 | David et al. |
| 5,092,839 A | 3/1992 | Kipperman |
| 5,100,423 A | 3/1992 | Fearnot |
| 5,102,415 A | 4/1992 | Guenther et al. |
| 5,108,419 A | 4/1992 | Reger et al. |
| 5,122,136 A | 6/1992 | Guglielmi et al. |
| 5,163,951 A | 11/1992 | Pinchuk et al. |
| 5,171,233 A | 12/1992 | Amplatz et al. |
| 5,171,259 A | 12/1992 | Inoue |
| 5,217,441 A | 6/1993 | Shichman |
| 5,234,437 A | 8/1993 | Sepetka |
| 5,236,447 A | 8/1993 | Kubo et al. |
| 5,330,482 A | 7/1994 | Gibbs et al. |
| 5,383,887 A | 1/1995 | Nadal |
| 5,387,219 A | 2/1995 | Rappe |
| 5,387,226 A | 2/1995 | Miraki |
| 5,449,372 A | 9/1995 | Schmaltz et al. |
| 5,499,985 A | 3/1996 | Hein et al. |
| 5,538,512 A | 7/1996 | Zenzon et al. |
| 5,538,515 A | 7/1996 | Kafry et al. |
| 5,549,626 A | 8/1996 | Miller et al. |
| 5,558,652 A | 9/1996 | Henke |
| 5,609,627 A | 3/1997 | Goicoechea et al. |
| 5,624,461 A | 4/1997 | Mariant |
| 5,639,277 A | 6/1997 | Mariant et al. |
| 5,639,278 A | 6/1997 | Dereume et al. |
| 5,645,558 A | 7/1997 | Horton |
| 5,653,605 A | 8/1997 | Woehl et al. |
| 5,658,296 A | 8/1997 | Bates et al. |
| 5,665,117 A | 9/1997 | Rhodes |
| 5,695,519 A | 12/1997 | Summers et al. |
| 5,709,704 A | 1/1998 | Nott et al. |
| 5,713,853 A | 2/1998 | Clark et al. |
| 5,769,871 A | 6/1998 | Mers Kelly et al. |
| 5,769,884 A | 6/1998 | Solovay |
| 5,779,686 A | 7/1998 | Sato et al. |
| 5,779,716 A | 7/1998 | Cano et al. |
| 5,800,519 A | 9/1998 | Sandock |
| 5,810,874 A | 9/1998 | Lefebvre |
| 5,814,064 A | 9/1998 | Daniel et al. |
| 5,827,304 A | 10/1998 | Hart |
| 5,853,422 A | 12/1998 | Huebsch et al. |
| 5,855,598 A | 1/1999 | Pinchuk |
| 5,893,869 A | 4/1999 | Barnhart et al. |
| 5,895,398 A | 4/1999 | Wensel et al. |
| 5,897,567 A | 4/1999 | Ressemann et al. |
| 5,904,698 A | 5/1999 | Thomas et al. |
| 5,911,702 A | 6/1999 | Romley et al. |
| 5,911,725 A | 6/1999 | Boury |
| 5,919,126 A | 7/1999 | Armini |
| 5,931,509 A | 8/1999 | Bartholomew |
| 5,935,139 A | 8/1999 | Bates |
| 5,947,995 A | 9/1999 | Samuels |
| 6,063,113 A | 5/2000 | Kavteladze et al. |
| 6,066,149 A | 5/2000 | Samson et al. |
| 6,066,158 A | 5/2000 | Engelson et al. |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates et al. |
| 6,099,559 A | 8/2000 | Nolting |
| 6,102,932 A | 8/2000 | Kurz |
| 6,106,548 A | 8/2000 | Roubin et al. |
| 6,129,739 A | 10/2000 | Khosravi |
| 6,143,022 A | 11/2000 | Shull et al. |
| 6,146,404 A | 11/2000 | Kim et al. |
| 6,156,064 A | 12/2000 | Chouinard |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,221,006 B1 | 4/2001 | Dubrul et al. |
| 6,221,096 B1 | 4/2001 | Aiba et al. |
| 6,231,597 B1 | 5/2001 | Deem et al. |
| 6,238,412 B1 | 5/2001 | Dubrul et al. |
| 6,245,012 B1 | 6/2001 | Kleshinski |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,267,777 B1 | 7/2001 | Bosma et al. |
| 6,290,710 B1 | 9/2001 | Cryer et al. |
| 6,312,444 B1 | 11/2001 | Barbut |
| 6,315,778 B1 | 11/2001 | Gambale et al. |
| 6,325,815 B1 | 12/2001 | Kusleika et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,346,116 B1 | 2/2002 | Brooks et al. |
| 6,348,056 B1 | 2/2002 | Bates et al. |
| 6,350,271 B1 | 2/2002 | Kurz et al. |
| 6,355,057 B1 | 3/2002 | DeMarais et al. |
| 6,361,545 B1 | 3/2002 | Macoviak et al. |
| 6,364,895 B1 | 4/2002 | Greenhalgh |
| 6,375,668 B1 | 4/2002 | Gifford et al. |
| 6,375,670 B1 | 4/2002 | Greenhalgh |
| 6,383,205 B1 | 5/2002 | Samson et al. |
| 6,383,206 B1 | 5/2002 | Gillick et al. |
| 6,391,037 B1 | 5/2002 | Greenhalgh |
| 6,402,771 B1 | 6/2002 | Palmer et al. |
| 6,416,541 B2 | 7/2002 | Denardo |
| 6,425,909 B1 | 7/2002 | Dieck et al. |
| 6,428,558 B1 | 8/2002 | Jones et al. |
| 6,432,122 B1 | 8/2002 | Gilson et al. |
| 6,436,112 B2 | 8/2002 | Wensel et al. |
| 6,458,139 B1 | 10/2002 | Palmer et al. |
| 6,485,497 B2 | 11/2002 | Wensel et al. |
| 6,485,501 B1 | 11/2002 | Green |
| 6,485,502 B2 | 11/2002 | Don Michael et al. |
| 6,488,701 B1 | 12/2002 | Nolting et al. |
| 6,511,492 B1 | 1/2003 | Rosenbluth et al. |
| 6,530,935 B2 | 3/2003 | Wensel et al. |
| 6,530,939 B1 | 3/2003 | Hopkins et al. |
| 6,540,768 B1 | 4/2003 | Diaz et al. |
| 6,544,279 B1 | 4/2003 | Hopkins et al. |
| 6,551,341 B2 | 4/2003 | Boylan et al. |
| 6,551,342 B1 | 4/2003 | Shen et al. |
| 6,575,996 B1 | 6/2003 | Denison et al. |
| 6,575,997 B1 | 6/2003 | Palmer et al. |
| 6,582,448 B1 | 6/2003 | Boyle et al. |
| 6,585,756 B1 | 7/2003 | Strecker |
| 6,589,265 B1 | 7/2003 | Palmer et al. |
| 6,592,607 B1 | 7/2003 | Palmer et al. |
| 6,592,614 B2 | 7/2003 | Lenker et al. |
| 6,592,616 B1 | 7/2003 | Stack et al. |
| 6,598,265 B2 | 7/2003 | Lee |
| 6,602,265 B2 | 8/2003 | Dubrul et al. |
| 6,602,271 B2 | 8/2003 | Adams et al. |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,632,241 B1 | 10/2003 | Hancock et al. |
| 6,638,245 B2 | 10/2003 | Miller et al. |
| 6,638,293 B1 | 10/2003 | Makower et al. |
| 6,641,590 B1 | 11/2003 | Palmer et al. |
| 6,656,218 B1 | 12/2003 | Denardo et al. |

(56) References Cited

U.S. PATENT DOCUMENTS

| | | |
|---|---|---|
| 6,660,021 B1 | 12/2003 | Palmer et al. |
| 6,663,650 B2 | 12/2003 | Sepetka et al. |
| 6,673,089 B1 | 1/2004 | Yassour et al. |
| 6,685,722 B1 | 2/2004 | Rosenbluth et al. |
| 6,692,504 B2 | 2/2004 | Kurz et al. |
| 6,692,508 B2 | 2/2004 | Wensel et al. |
| 6,692,509 B2 | 2/2004 | Wensel et al. |
| 6,695,858 B1 | 2/2004 | Dubrul et al. |
| 6,702,782 B2 | 3/2004 | Miller et al. |
| 6,702,834 B1 | 3/2004 | Boylan et al. |
| 6,709,465 B2 | 3/2004 | Mitchell et al. |
| 6,712,834 B2 | 3/2004 | Yassour et al. |
| 6,726,701 B2 | 4/2004 | Gilson et al. |
| 6,726,703 B2 | 4/2004 | Broome et al. |
| 6,730,104 B1 | 5/2004 | Sepetka et al. |
| 6,783,528 B2 | 8/2004 | Vincent-Prestigiacomo |
| 6,783,538 B2 | 8/2004 | McGuckin, Jr. et al. |
| 6,824,545 B2 | 11/2004 | Sepetka et al. |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer et al. |
| 6,913,618 B2 | 7/2005 | Denardo et al. |
| 6,939,361 B1 | 9/2005 | Kleshinski |
| 6,953,472 B2 | 10/2005 | Palmer et al. |
| 6,989,019 B2 | 1/2006 | Mazzocchi et al. |
| 6,989,021 B2 | 1/2006 | Bosma et al. |
| 6,994,718 B2 | 2/2006 | Groothuis et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,008,434 B2 | 3/2006 | Kurz et al. |
| 7,033,376 B2 | 4/2006 | Tsukernik |
| 7,041,116 B2 | 5/2006 | Goto et al. |
| 7,048,758 B2 | 5/2006 | Boyle et al. |
| 7,052,500 B2 | 5/2006 | Bashiri et al. |
| 7,058,456 B2 | 6/2006 | Pierce |
| 7,063,707 B2 | 6/2006 | Bose et al. |
| 7,083,633 B2 | 8/2006 | Morrill et al. |
| 7,083,822 B2 | 8/2006 | Brightbill |
| 7,094,249 B1 | 8/2006 | Broome et al. |
| 7,097,653 B2 | 8/2006 | Freudenthal et al. |
| 7,101,380 B2 | 9/2006 | Khachin et al. |
| 7,172,614 B2 | 2/2007 | Boyle et al. |
| 7,175,655 B1 | 2/2007 | Molaei |
| 7,179,273 B1 | 2/2007 | Palmer et al. |
| 7,185,922 B2 | 3/2007 | Takayanagi et al. |
| 7,220,271 B2 | 5/2007 | Clubb et al. |
| 7,226,464 B2 | 6/2007 | Garner et al. |
| 7,229,472 B2 | 6/2007 | DePalma et al. |
| 7,241,304 B2 | 7/2007 | Boyle et al. |
| 7,288,112 B2 | 10/2007 | Denardo et al. |
| 7,300,458 B2 | 11/2007 | Henkes et al. |
| 7,306,618 B2 | 12/2007 | Demond et al. |
| 7,314,483 B2 | 1/2008 | Landau et al. |
| 7,316,692 B2 | 1/2008 | Huffmaster |
| 7,323,001 B2 | 1/2008 | Clubb et al. |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins et al. |
| 7,425,215 B2 | 9/2008 | Boyle et al. |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka et al. |
| 7,556,636 B2 | 7/2009 | Mazzocchi et al. |
| 7,582,111 B2 | 9/2009 | Krolik et al. |
| 7,594,926 B2 | 9/2009 | Linder et al. |
| 7,604,649 B2 | 10/2009 | McGuckin, Jr. et al. |
| 7,604,650 B2 | 10/2009 | Bergheim |
| 7,609,649 B1 | 10/2009 | Bhandari et al. |
| 7,618,434 B2 | 11/2009 | Santra et al. |
| 7,662,165 B2 | 2/2010 | Gilson et al. |
| 7,670,356 B2 | 3/2010 | Mazzocchi et al. |
| 7,678,123 B2 | 3/2010 | Chanduszko |
| 7,691,121 B2 | 4/2010 | Rosenbluth et al. |
| 7,691,124 B2 | 4/2010 | Balgobin |
| 7,708,770 B2 | 5/2010 | Linder et al. |
| 7,717,929 B2 | 5/2010 | Fallman |
| 7,736,385 B2 | 6/2010 | Agnew |
| 7,749,246 B2 | 7/2010 | McGuckin, Jr. et al. |
| 7,758,606 B2 | 7/2010 | Streeter et al. |
| 7,758,611 B2 | 7/2010 | Kato |
| 7,766,934 B2 | 8/2010 | Pal et al. |
| 7,771,452 B2 | 8/2010 | Pal et al. |
| 7,780,694 B2 | 8/2010 | Palmer et al. |
| 7,780,700 B2 | 8/2010 | Frazier et al. |
| 7,811,305 B2 | 10/2010 | Balgobin et al. |
| 7,815,659 B2 | 10/2010 | Conlon et al. |
| 7,819,893 B2 | 10/2010 | Brady et al. |
| 7,828,815 B2 | 11/2010 | Mazzocchi et al. |
| 7,828,816 B2 | 11/2010 | Mazzocchi et al. |
| 7,833,240 B2 | 11/2010 | Okushi et al. |
| 7,842,053 B2 | 11/2010 | Chanduszko et al. |
| 7,846,175 B2 | 12/2010 | Bonnette et al. |
| 7,846,176 B2 | 12/2010 | Gilson et al. |
| 7,850,708 B2 | 12/2010 | Pal |
| 7,883,516 B2 | 2/2011 | Huang et al. |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi et al. |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | OBrien et al. |
| 8,052,640 B2 | 11/2011 | Fiorella et al. |
| 8,057,497 B1 | 11/2011 | Raju et al. |
| 8,057,507 B2 | 11/2011 | Horan et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,118,856 B2 | 2/2012 | Schreck et al. |
| 8,123,769 B2 | 2/2012 | Osborne |
| 8,137,376 B2 | 3/2012 | Clubb et al. |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,262,689 B2 | 9/2012 | Schneiderman et al. |
| 8,282,668 B2 | 10/2012 | McGuckin, Jr. et al. |
| 8,287,538 B2 | 10/2012 | Brenzel et al. |
| 8,298,257 B2 | 10/2012 | Sepetka et al. |
| RE43,882 E | 12/2012 | Hopkins et al. |
| 8,357,178 B2 | 1/2013 | Grandfield et al. |
| 8,357,179 B2 | 1/2013 | Grandfield et al. |
| 8,357,180 B2 | 1/2013 | Feller, III et al. |
| 8,357,893 B2 | 1/2013 | Xu et al. |
| 8,361,095 B2 | 1/2013 | Osborne |
| 8,361,110 B2 | 1/2013 | Chanduszko |
| 8,366,663 B2 | 2/2013 | Fiorella et al. |
| 8,409,215 B2 | 4/2013 | Sepetka et al. |
| 8,414,482 B2 | 4/2013 | Belson |
| 8,414,543 B2 | 4/2013 | McGuckin, Jr. et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,512,352 B2 | 8/2013 | Martin |
| 8,529,596 B2 | 9/2013 | Grandfield et al. |

(56) References Cited

U.S. PATENT DOCUMENTS

| | | |
|---|---|---|
| 8,545,526 B2 | 10/2013 | Martin et al. |
| 8,574,262 B2 | 11/2013 | Ferrera et al. |
| 8,574,915 B2 | 11/2013 | Zhang et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,690,907 B1 | 4/2014 | Janardhan et al. |
| 8,696,622 B2 | 4/2014 | Fiorella et al. |
| 8,702,652 B2 | 4/2014 | Fiorella et al. |
| 8,702,704 B2 | 4/2014 | Shelton, IV et al. |
| 8,702,724 B2 | 4/2014 | Olsen et al. |
| 8,777,919 B2 | 7/2014 | Kimura et al. |
| 8,777,976 B2 | 7/2014 | Brady et al. |
| 8,777,979 B2 | 7/2014 | Shrivastava et al. |
| 8,784,434 B2 | 7/2014 | Rosenbluth et al. |
| 8,784,441 B2 | 7/2014 | Rosenbluth et al. |
| 8,795,305 B2 | 8/2014 | Martin et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,852,205 B2 | 10/2014 | Brady et al. |
| 8,870,941 B2 | 10/2014 | Evans et al. |
| 8,900,265 B1 | 12/2014 | Ulm, III |
| 8,920,358 B2 | 12/2014 | Levine et al. |
| 8,939,991 B2 | 1/2015 | Krolik et al. |
| 8,945,143 B2 | 2/2015 | Ferrera et al. |
| 8,945,160 B2 | 2/2015 | Krolik et al. |
| 8,945,169 B2 | 2/2015 | Pal |
| 8,945,172 B2 | 2/2015 | Ferrera et al. |
| 8,956,399 B2 | 2/2015 | Cam et al. |
| 8,968,330 B2 | 3/2015 | Rosenbluth et al. |
| 9,011,481 B2 | 4/2015 | Aggerholm et al. |
| 9,039,749 B2 | 5/2015 | Shrivastava et al. |
| 9,072,537 B2 | 7/2015 | Grandfield et al. |
| 9,095,342 B2 | 8/2015 | Becking et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,758 B2 | 10/2015 | Figulla et al. |
| 9,161,766 B2 | 10/2015 | Slee et al. |
| 9,173,668 B2 | 11/2015 | Ulm, III |
| 9,173,688 B2 | 11/2015 | Dosta |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,211,132 B2 | 12/2015 | Bowman |
| 9,232,992 B2 | 1/2016 | Heidner et al. |
| 9,254,371 B2 | 2/2016 | Martin et al. |
| 9,301,769 B2 | 4/2016 | Brady et al. |
| 9,332,999 B2 | 5/2016 | Ray et al. |
| 9,402,707 B2 | 8/2016 | Brady et al. |
| 9,445,829 B2 | 9/2016 | Brady et al. |
| 9,456,834 B2 | 10/2016 | Folk |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,639 B2 | 5/2017 | Brady et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,898 B2 | 5/2017 | Palepu et al. |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,758,606 B2 | 9/2017 | Lambert et al. |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,651 B2 | 10/2017 | Harrah et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,304 B2 | 12/2017 | Horan et al. |
| 9,833,604 B2 | 12/2017 | Lam et al. |
| 9,833,625 B2 | 12/2017 | Waldhauser et al. |
| 9,901,434 B2 | 2/2018 | Hoffman |
| 9,918,720 B2 | 3/2018 | Marchand et al. |
| 9,939,361 B2 | 4/2018 | Gajji et al. |
| 10,016,206 B1 | 7/2018 | Yang |
| 10,070,878 B2 | 9/2018 | Ma |
| 10,098,651 B2 | 10/2018 | Marchand et al. |
| 10,201,360 B2 | 2/2019 | Vale et al. |
| 10,231,751 B2 | 3/2019 | Sos |
| 10,292,723 B2 | 5/2019 | Brady et al. |
| 10,299,811 B2 | 5/2019 | Brady et al. |
| 10,363,054 B2 | 7/2019 | Vale et al. |
| 10,376,274 B2 | 8/2019 | Farin et al. |
| 10,390,850 B2 | 8/2019 | Vale et al. |
| 10,524,811 B2 | 1/2020 | Marchand et al. |
| 10,531,942 B2 | 1/2020 | Eggers |
| 10,617,435 B2 | 4/2020 | Vale et al. |
| 10,722,257 B2 | 7/2020 | Skillrud et al. |
| 11,517,340 B2 | 12/2022 | Casey |
| 2001/0001315 A1 | 5/2001 | Bates et al. |
| 2001/0016755 A1 | 8/2001 | Addis |
| 2001/0037141 A1 | 11/2001 | Yee et al. |
| 2001/0037171 A1 | 11/2001 | Sato |
| 2001/0041909 A1 | 11/2001 | Tsugita et al. |
| 2001/0044632 A1 | 11/2001 | Daniel et al. |
| 2001/0049554 A1 | 12/2001 | Ruiz et al. |
| 2001/0051810 A1 | 12/2001 | Dubrul et al. |
| 2002/0004667 A1 | 1/2002 | Adams et al. |
| 2002/0016609 A1 | 2/2002 | Wensel et al. |
| 2002/0022859 A1 | 2/2002 | Hogendijk |
| 2002/0026211 A1 | 2/2002 | Khosravi et al. |
| 2002/0042627 A1 | 4/2002 | Brady et al. |
| 2002/0049468 A1 | 4/2002 | Streeter et al. |
| 2002/0052620 A1 | 5/2002 | Barbut |
| 2002/0058911 A1 | 5/2002 | Gilson et al. |
| 2002/0068954 A1 | 6/2002 | Foster |
| 2002/0072764 A1 | 6/2002 | Sepetka et al. |
| 2002/0082558 A1 | 6/2002 | Samson et al. |
| 2002/0091407 A1 | 7/2002 | Zadno-Azizi et al. |
| 2002/0095171 A1 | 7/2002 | Belef |

(56) References Cited

U.S. PATENT DOCUMENTS

| | | |
|---|---|---|
| 2002/0123765 A1 | 9/2002 | Sepetka et al. |
| 2002/0128680 A1 | 9/2002 | Pavolvic |
| 2002/0138094 A1 | 9/2002 | Borillo et al. |
| 2002/0143349 A1 | 10/2002 | Ill et al. |
| 2002/0143362 A1 | 10/2002 | Macoviak et al. |
| 2002/0156455 A1 | 10/2002 | Barbut |
| 2002/0161393 A1 | 10/2002 | Demond et al. |
| 2002/0165576 A1 | 11/2002 | Boyle et al. |
| 2002/0173819 A1 | 11/2002 | Leeflang et al. |
| 2002/0183787 A1 | 12/2002 | Wahr et al. |
| 2002/0188276 A1 | 12/2002 | Evans et al. |
| 2002/0188314 A1 | 12/2002 | Anderson et al. |
| 2002/0193824 A1 | 12/2002 | Boylan et al. |
| 2002/0198588 A1 | 12/2002 | Armstrong et al. |
| 2003/0004536 A1 | 1/2003 | Boylan et al. |
| 2003/0004538 A1 | 1/2003 | Secrest et al. |
| 2003/0004540 A1 | 1/2003 | Linder et al. |
| 2003/0004542 A1 | 1/2003 | Wensel et al. |
| 2003/0009146 A1 | 1/2003 | Muni et al. |
| 2003/0009191 A1 | 1/2003 | Wensel et al. |
| 2003/0038447 A1 | 2/2003 | Cantele |
| 2003/0040772 A1 | 2/2003 | Hyodoh et al. |
| 2003/0050663 A1 | 3/2003 | Khachin et al. |
| 2003/0064151 A1 | 4/2003 | Klinedinst |
| 2003/0108224 A1 | 6/2003 | Ike |
| 2003/0114879 A1 | 6/2003 | Euteneuer et al. |
| 2003/0125798 A1 | 7/2003 | Martin |
| 2003/0130682 A1 | 7/2003 | Broome et al. |
| 2003/0144687 A1 | 7/2003 | Brady et al. |
| 2003/0144688 A1 | 7/2003 | Brady et al. |
| 2003/0153158 A1 | 8/2003 | Ho et al. |
| 2003/0153943 A1 | 8/2003 | Michael et al. |
| 2003/0153944 A1 | 8/2003 | Phung et al. |
| 2003/0163064 A1 | 8/2003 | Vrba et al. |
| 2003/0163158 A1 | 8/2003 | White |
| 2003/0171769 A1 | 9/2003 | Barbut |
| 2003/0171771 A1 | 9/2003 | Anderson et al. |
| 2003/0176884 A1 | 9/2003 | Berrada et al. |
| 2003/0187495 A1 | 10/2003 | Cully et al. |
| 2003/0195537 A1 | 10/2003 | Dubrul et al. |
| 2003/0195554 A1 | 10/2003 | Shen et al. |
| 2003/0199917 A1 | 10/2003 | Knudson et al. |
| 2003/0204202 A1 | 10/2003 | Palmer et al. |
| 2003/0208224 A1 | 11/2003 | Broome |
| 2003/0212430 A1 | 11/2003 | Bose et al. |
| 2003/0236533 A1 | 12/2003 | Wilson et al. |
| 2004/0064179 A1 | 4/2004 | Linder et al. |
| 2004/0068288 A1 | 4/2004 | Palmer et al. |
| 2004/0073243 A1 | 4/2004 | Sepetka et al. |
| 2004/0079429 A1 | 4/2004 | Miller et al. |
| 2004/0082962 A1 | 4/2004 | Demarais et al. |
| 2004/0082967 A1 | 4/2004 | Broome et al. |
| 2004/0088001 A1 | 5/2004 | Bosma et al. |
| 2004/0093065 A1 | 5/2004 | Yachia et al. |
| 2004/0098050 A1 | 5/2004 | Foerster et al. |
| 2004/0133231 A1 | 7/2004 | Maitland et al. |
| 2004/0133232 A1 | 7/2004 | Rosenbluth et al. |
| 2004/0138692 A1 | 7/2004 | Phung et al. |
| 2004/0153117 A1 | 8/2004 | Clubb et al. |
| 2004/0153118 A1 | 8/2004 | Clubb et al. |
| 2004/0199201 A1 | 10/2004 | Kellett et al. |
| 2004/0215318 A1 | 10/2004 | Kwitkin |
| 2004/0220663 A1 | 11/2004 | Rivelli |
| 2005/0033248 A1 | 2/2005 | Machida et al. |
| 2005/0033348 A1 | 2/2005 | Sepetka et al. |
| 2005/0038447 A1 | 2/2005 | Huffmaster |
| 2005/0038468 A1 | 2/2005 | Panetta et al. |
| 2005/0043759 A1 | 2/2005 | Chanduszko |
| 2005/0049619 A1 | 3/2005 | Sepetka et al. |
| 2005/0049669 A1 | 3/2005 | Jones et al. |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0058837 A1 | 3/2005 | Farnworth et al. |
| 2005/0059995 A1 | 3/2005 | Sepetka et al. |
| 2005/0085849 A1 | 4/2005 | Sepetka et al. |
| 2005/0090779 A1 | 4/2005 | Osypka |
| 2005/0090857 A1 | 4/2005 | Kusleika et al. |
| 2005/0125024 A1 | 6/2005 | Sepetka et al. |
| 2005/0149997 A1 | 7/2005 | Wolozin et al. |
| 2005/0171566 A1 | 8/2005 | Kanamaru |
| 2005/0173135 A1 | 8/2005 | Almen |
| 2005/0192627 A1 | 9/2005 | Whisenant et al. |
| 2005/0215942 A1 | 9/2005 | Abrahamson et al. |
| 2005/0216030 A1 | 9/2005 | Sepetka et al. |
| 2005/0216050 A1 | 9/2005 | Sepetka et al. |
| 2005/0228417 A1 | 10/2005 | Teitelbaum et al. |
| 2005/0251206 A1 | 11/2005 | Maahs et al. |
| 2005/0251209 A1 | 11/2005 | Saadat et al. |
| 2005/0267491 A1 | 12/2005 | Kellett et al. |
| 2005/0273135 A1 | 12/2005 | Chanduszko et al. |
| 2005/0283186 A1 | 12/2005 | Berrada et al. |
| 2005/0288686 A1 | 12/2005 | Sepetka et al. |
| 2006/0008332 A1 | 1/2006 | Greenberg et al. |
| 2006/0009798 A1 | 1/2006 | Callister et al. |
| 2006/0009799 A1 | 1/2006 | Kleshinski et al. |
| 2006/0020285 A1 | 1/2006 | Niermann |
| 2006/0020286 A1 | 1/2006 | Niermann |
| 2006/0030877 A1 | 2/2006 | Martinez et al. |
| 2006/0041228 A1 | 2/2006 | Vo et al. |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0064151 A1 | 3/2006 | Guterman et al. |
| 2006/0069424 A1 | 3/2006 | Acosta et al. |
| 2006/0074477 A1 | 4/2006 | Berthiaume et al. |
| 2006/0149313 A1 | 7/2006 | Arguello et al. |
| 2006/0155305 A1 | 7/2006 | Freudenthal et al. |
| 2006/0161187 A1 | 7/2006 | Evine et al. |
| 2006/0195137 A1 | 8/2006 | Sepetka et al. |
| 2006/0224177 A1 | 10/2006 | Finitsis |
| 2006/0224179 A1 | 10/2006 | Kucharczyk et al. |
| 2006/0229638 A1 | 10/2006 | Abrams et al. |
| 2006/0235501 A1 | 10/2006 | Igaki |
| 2006/0241677 A1 | 10/2006 | Johnson et al. |
| 2006/0282111 A1 | 12/2006 | Morsi |
| 2006/0287668 A1 | 12/2006 | Fawzi et al. |
| 2006/0287701 A1 | 12/2006 | Pal |
| 2006/0293706 A1 | 12/2006 | Shimon |
| 2007/0010857 A1 | 1/2007 | Sugimoto et al. |
| 2007/0032879 A1 | 2/2007 | Levine et al. |
| 2007/0088382 A1 | 4/2007 | Bei et al. |
| 2007/0088383 A1 | 4/2007 | Pal et al. |
| 2007/0100348 A1 | 5/2007 | Cauthen, III et al. |
| 2007/0118173 A1 | 5/2007 | Magnuson et al. |
| 2007/0149997 A1 | 6/2007 | Muller |
| 2007/0156170 A1 | 7/2007 | Hancock et al. |
| 2007/0165170 A1 | 7/2007 | Fukuda |
| 2007/0179527 A1 | 8/2007 | Eskuri et al. |
| 2007/0191866 A1 | 8/2007 | Palmer et al. |
| 2007/0198028 A1 | 8/2007 | Miloslavski et al. |
| 2007/0198051 A1 | 8/2007 | Clubb et al. |
| 2007/0198075 A1 | 8/2007 | Levy |
| 2007/0208367 A1 | 9/2007 | Fiorella et al. |
| 2007/0208371 A1 | 9/2007 | French et al. |
| 2007/0225749 A1 | 9/2007 | Martin et al. |
| 2007/0233175 A1 | 10/2007 | Zaver et al. |
| 2007/0244505 A1 | 10/2007 | Gilson et al. |
| 2007/0270902 A1 | 11/2007 | Slazas et al. |
| 2007/0288054 A1 | 12/2007 | Tanaka et al. |
| 2008/0045881 A1 | 2/2008 | Teitelbaum et al. |
| 2008/0077227 A1 | 3/2008 | Ouellette et al. |
| 2008/0082107 A1 | 4/2008 | Miller et al. |
| 2008/0086190 A1 | 4/2008 | Ta |
| 2008/0091223 A1 | 4/2008 | Pokorney et al. |
| 2008/0097386 A1 | 4/2008 | Osypka |
| 2008/0109031 A1 | 5/2008 | Sepetka et al. |
| 2008/0109032 A1 | 5/2008 | Sepetka et al. |
| 2008/0119886 A1 | 5/2008 | Greenhalgh et al. |
| 2008/0125798 A1 | 5/2008 | Osborne et al. |
| 2008/0177296 A1 | 7/2008 | Sepetka et al. |
| 2008/0178890 A1 | 7/2008 | Townsend et al. |
| 2008/0183197 A1 | 7/2008 | Sepetka et al. |
| 2008/0183198 A1 | 7/2008 | Sepetka et al. |

(56) References Cited

U.S. PATENT DOCUMENTS

| | | |
|---|---|---|
| 2008/0183205 A1 | 7/2008 | Sepetka et al. |
| 2008/0188876 A1 | 8/2008 | Sepetka et al. |
| 2008/0188885 A1 | 8/2008 | Sepetka et al. |
| 2008/0188887 A1 | 8/2008 | Batiste |
| 2008/0200946 A1 | 8/2008 | Braun et al. |
| 2008/0200947 A1 | 8/2008 | Kusleika et al. |
| 2008/0215077 A1 | 9/2008 | Sepetka et al. |
| 2008/0221600 A1 | 9/2008 | Dieck et al. |
| 2008/0228209 A1 | 9/2008 | DeMello et al. |
| 2008/0234706 A1 | 9/2008 | Sepetka et al. |
| 2008/0243170 A1 | 10/2008 | Jenson et al. |
| 2008/0255596 A1 | 10/2008 | Jenson et al. |
| 2008/0262410 A1 | 10/2008 | Jenson et al. |
| 2008/0262528 A1 | 10/2008 | Martin |
| 2008/0262532 A1 | 10/2008 | Martin |
| 2008/0269871 A1 | 10/2008 | Eli |
| 2008/0275488 A1 | 11/2008 | Fleming |
| 2008/0275493 A1 | 11/2008 | Farmiga |
| 2008/0281350 A1 | 11/2008 | Sepetka et al. |
| 2008/0312681 A1 | 12/2008 | Ansel et al. |
| 2009/0005858 A1 | 1/2009 | Young et al. |
| 2009/0024157 A1 | 1/2009 | Anukhin |
| 2009/0030443 A1 | 1/2009 | Buser et al. |
| 2009/0062841 A1 | 3/2009 | Amplatz et al. |
| 2009/0069828 A1 | 3/2009 | Martin et al. |
| 2009/0076539 A1 | 3/2009 | Valaie |
| 2009/0088793 A1 | 4/2009 | Bagaoisan et al. |
| 2009/0088795 A1 | 4/2009 | Cahill |
| 2009/0105722 A1 | 4/2009 | Fulkerson et al. |
| 2009/0105737 A1 | 4/2009 | Fulkerson et al. |
| 2009/0105747 A1 | 4/2009 | Chanduszko et al. |
| 2009/0149881 A1 | 6/2009 | Vale et al. |
| 2009/0163851 A1 | 6/2009 | Holloway et al. |
| 2009/0177206 A1 | 7/2009 | Lozier et al. |
| 2009/0182336 A1 | 7/2009 | Brenzel et al. |
| 2009/0281610 A1 | 11/2009 | Parker |
| 2009/0281619 A1 | 11/2009 | Le et al. |
| 2009/0287229 A1 | 11/2009 | Ogdahl |
| 2009/0292297 A1 | 11/2009 | Ferrere |
| 2009/0292307 A1 | 11/2009 | Razack |
| 2009/0299393 A1 | 12/2009 | Martin et al. |
| 2009/0299403 A1 | 12/2009 | Chanduszko et al. |
| 2009/0306702 A1 | 12/2009 | Miloslavski et al. |
| 2009/0326636 A1 | 12/2009 | Hashimoto et al. |
| 2010/0004607 A1 | 1/2010 | Wilson et al. |
| 2010/0076482 A1 | 3/2010 | Shu et al. |
| 2010/0087850 A1 | 4/2010 | Razack |
| 2010/0087908 A1 | 4/2010 | Hilaire et al. |
| 2010/0114017 A1 | 5/2010 | Lenker et al. |
| 2010/0125326 A1 | 5/2010 | Kalstad et al. |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnette et al. |
| 2010/0268265 A1 | 10/2010 | Krolik et al. |
| 2010/0274277 A1 | 10/2010 | Eaton |
| 2010/0318178 A1 | 12/2010 | Rapaport et al. |
| 2010/0324649 A1 | 12/2010 | Mattsson et al. |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009950 A1 | 1/2011 | Grandfield et al. |
| 2011/0015718 A1 | 1/2011 | Schreck |
| 2011/0022149 A1 | 1/2011 | Cox et al. |
| 2011/0040319 A1 | 2/2011 | Fulton, III |
| 2011/0054287 A1* | 3/2011 | Schultz ............. A61M 25/0147 604/95.04 |
| 2011/0054504 A1 | 3/2011 | Porter |
| 2011/0054514 A1 | 3/2011 | Arcand et al. |
| 2011/0054516 A1 | 3/2011 | Keegan et al. |
| 2011/0060212 A1 | 3/2011 | Slee et al. |
| 2011/0060359 A1 | 3/2011 | Hannes et al. |
| 2011/0106137 A1 | 5/2011 | Shimon |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0184456 A1 | 7/2011 | Grandfield et al. |
| 2011/0196414 A1 | 8/2011 | Porter et al. |
| 2011/0202088 A1 | 8/2011 | Eckhouse et al. |
| 2011/0208233 A1 | 8/2011 | McGuckin, Jr. et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0224707 A1 | 9/2011 | Miloslavski et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | di Palma et al. |
| 2012/0065660 A1 | 3/2012 | Ferrera et al. |
| 2012/0083823 A1 | 4/2012 | Shrivastava et al. |
| 2012/0083868 A1 | 4/2012 | Shrivastava et al. |
| 2012/0089216 A1 | 4/2012 | Rapaport et al. |
| 2012/0101510 A1 | 4/2012 | Lenker et al. |
| 2012/0116440 A1 | 5/2012 | Leynov et al. |
| 2012/0123466 A1 | 5/2012 | Porter et al. |
| 2012/0022572 A1 | 6/2012 | Braun et al. |
| 2012/0143230 A1 | 6/2012 | Sepetka et al. |
| 2012/0143237 A1 | 6/2012 | Cam et al. |
| 2012/0143317 A1 | 6/2012 | Cam et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0209312 A1 | 8/2012 | Aggerholm et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2012/0330350 A1 | 12/2012 | Jones et al. |
| 2013/0030460 A1 | 1/2013 | Marks et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144311 A1 | 6/2013 | Fung et al. |
| 2013/0144326 A1 | 6/2013 | Brady et al. |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0271788 A1 | 10/2013 | Utsunomiya |
| 2013/0277079 A1 | 10/2013 | Tsuzuki et al. |
| 2013/0281788 A1 | 10/2013 | Garrison |
| 2013/0325051 A1 | 12/2013 | Martin et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0046359 A1 | 2/2014 | Bowman et al. |
| 2014/0088678 A1 | 3/2014 | Wainwright et al. |
| 2014/0121672 A1 | 5/2014 | Folk |
| 2014/0128905 A1 | 5/2014 | Molaei |
| 2014/0134654 A1 | 5/2014 | Rudel et al. |
| 2014/0135812 A1 | 5/2014 | Divino et al. |
| 2014/0142598 A1 | 5/2014 | Fulton, III |
| 2014/0163367 A1 | 6/2014 | Eskuri |
| 2014/0180122 A1 | 6/2014 | Stigall et al. |
| 2014/0180377 A1 | 6/2014 | Bose et al. |
| 2014/0180397 A1 | 6/2014 | Gerberding et al. |
| 2014/0183077 A1 | 7/2014 | Rosendall et al. |
| 2014/0194911 A1 | 7/2014 | Johnson et al. |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0243881 A1 | 8/2014 | Lees et al. |
| 2014/0257362 A1 | 9/2014 | Eidenschink |
| 2014/0276922 A1 | 9/2014 | McLain et al. |

(56) References Cited

U.S. PATENT DOCUMENTS

| | | |
|---|---|---|
| 2014/0277079 A1 | 9/2014 | Vale et al. |
| 2014/0303667 A1 | 10/2014 | Cox et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0372779 A1 | 12/2014 | Wong et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0032144 A1 | 1/2015 | Holloway |
| 2015/0080937 A1 | 3/2015 | Davidson |
| 2015/0112376 A1 | 4/2015 | Molaei et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0224133 A1 | 8/2015 | Ohri et al. |
| 2015/0250497 A1 | 9/2015 | Marks et al. |
| 2015/0257775 A1 | 9/2015 | Gilvarry et al. |
| 2015/0272716 A1 | 10/2015 | Pinchuk et al. |
| 2015/0297252 A1 | 10/2015 | Miloslavski et al. |
| 2015/0313617 A1 | 11/2015 | Grandfield et al. |
| 2015/0320431 A1 | 11/2015 | Ulm |
| 2015/0352325 A1 | 12/2015 | Quick |
| 2015/0359547 A1 | 12/2015 | Vale et al. |
| 2015/0366650 A1 | 12/2015 | Zi et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022269 A1 | 1/2016 | Ganske et al. |
| 2016/0022296 A1 | 1/2016 | Brady et al. |
| 2016/0045298 A1 | 2/2016 | Thinnes, Jr. et al. |
| 2016/0066921 A1 | 3/2016 | Seifert et al. |
| 2016/0100928 A1 | 4/2016 | Lees et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0303381 A1 | 10/2016 | Pierce et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020542 A1 | 1/2017 | Martin et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0056061 A1 | 3/2017 | Ogle et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0112647 A1 | 4/2017 | Sachar et al. |
| 2017/0113023 A1 | 4/2017 | Steingisser et al. |
| 2017/0119409 A1 | 5/2017 | Ma |
| 2017/0143465 A1 | 5/2017 | Ulm, III |
| 2017/0147765 A1 | 5/2017 | Mehta |
| 2017/0150979 A1 | 6/2017 | Ulm |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0189041 A1 | 7/2017 | Cox et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140315 A1 | 5/2018 | Bowman et al. |
| 2018/0206865 A1 | 7/2018 | Martin et al. |
| 2018/0207399 A1 | 7/2018 | Chou et al. |
| 2018/0263650 A1 | 9/2018 | Iwanami et al. |
| 2018/0325537 A1 | 11/2018 | Shamay et al. |
| 2018/0326024 A1 | 11/2018 | Prochazka et al. |
| 2018/0344338 A1 | 12/2018 | Brady et al. |
| 2019/0000492 A1 | 1/2019 | Casey et al. |
| 2019/0015061 A1 | 1/2019 | Liebeskind et al. |
| 2019/0167284 A1 | 6/2019 | Friedman et al. |
| 2019/0239907 A1 | 8/2019 | Brady et al. |
| 2019/0292273 A1 | 9/2019 | Hanotin et al. |
| 2019/0374239 A1 | 12/2019 | Martin et al. |
| 2019/0380723 A1 | 12/2019 | Grandfield et al. |
| 2019/0388097 A1 | 12/2019 | Girdhar et al. |

(56) References Cited

U.S. PATENT DOCUMENTS

| | | |
|---|---|---|
| 2020/0000483 A1 | 1/2020 | Brady et al. |
| 2020/0009150 A1 | 1/2020 | Chamorro Sanchez |
| 2020/0085444 A1 | 3/2020 | Vale et al. |
| 2020/0100804 A1 | 4/2020 | Casey et al. |
| 2020/0297364 A1 | 9/2020 | Choe et al. |
| 2020/0390459 A1 | 12/2020 | Casey et al. |
| 2021/0007757 A1 | 1/2021 | Casey et al. |
| 2021/0228223 A1 | 7/2021 | Casey et al. |

FOREIGN PATENT DOCUMENTS

| | | |
|---|---|---|
| CN | 102307613 A | 1/2012 |
| CN | 102316809 A | 1/2012 |
| CN | 102596098 A | 7/2012 |
| CN | 103764049 A | 4/2014 |
| CN | 104042304 A | 9/2014 |
| CN | 105208950 A | 12/2015 |
| CN | 105662532 A | 6/2016 |
| CN | 205359559 U | 7/2016 |
| CN | 107530090 A | 1/2018 |
| CN | 208582467 U | 3/2019 |
| DE | 202009001951 U1 | 3/2010 |
| DE | 102009056450 A1 | 6/2011 |
| DE | 102010010849 A1 | 9/2011 |
| DE | 102010014778 A1 | 10/2011 |
| DE | 102010024085 A1 | 12/2011 |
| DE | 102011014586 B3 | 9/2012 |
| EP | 1153581 A1 | 11/2001 |
| EP | 2301450 A1 | 3/2011 |
| EP | 2438891 A1 | 4/2012 |
| EP | 2628455 A1 | 8/2013 |
| EP | 3156004 A1 | 4/2017 |
| EP | 3593742 A1 | 1/2020 |
| EP | 3669802 A1 | 6/2020 |
| EP | 3858291 A1 | 8/2021 |
| GB | 2427554 A | 1/2007 |
| GB | 2494820 A | 3/2013 |
| JP | H0919438 A | 1/1997 |
| JP | 2014511223 A | 5/2014 |
| JP | 2014525796 A | 10/2014 |
| JP | 2015-505250 A | 2/2015 |
| JP | 2016-513505 A | 5/2016 |
| JP | 2019-526365 A | 9/2019 |
| WO | 9424926 A1 | 11/1994 |
| WO | 9727808 A1 | 8/1997 |
| WO | 9738631 A1 | 10/1997 |
| WO | 9920335 A1 | 4/1999 |
| WO | 9956801 A2 | 11/1999 |
| WO | 9960933 A1 | 12/1999 |
| WO | 0121077 A1 | 3/2001 |
| WO | 0202162 A2 | 1/2002 |
| WO | 0211627 A2 | 2/2002 |
| WO | 0243616 A2 | 6/2002 |
| WO | 02070061 A1 | 9/2002 |
| WO | 02094111 A2 | 11/2002 |
| WO | 03002006 A1 | 1/2003 |
| WO | 03030751 A1 | 4/2003 |
| WO | 03051448 A2 | 6/2003 |
| WO | 2004028571 A2 | 4/2004 |
| WO | 2004056275 A1 | 7/2004 |
| WO | 2005000130 A1 | 1/2005 |
| WO | 2005027779 A2 | 3/2005 |
| WO | 2006021407 A2 | 3/2006 |
| WO | 2006031410 A2 | 3/2006 |
| WO | 2006107641 A2 | 10/2006 |
| WO | 2006135823 A2 | 12/2006 |
| WO | 2007054307 A2 | 5/2007 |
| WO | 2007068424 A2 | 6/2007 |
| WO | 2008034615 A2 | 3/2008 |
| WO | 2008051431 A1 | 5/2008 |
| WO | 2008131116 A1 | 10/2008 |
| WO | 2008135823 A1 | 11/2008 |
| WO | 2009031338 A1 | 3/2009 |
| WO | 2009076482 A1 | 6/2009 |
| WO | 2009086482 A1 | 7/2009 |
| WO | 2009105710 A1 | 8/2009 |
| WO | 2010010545 A1 | 1/2010 |
| WO | 2010046897 A1 | 4/2010 |
| WO | 2010075565 A2 | 7/2010 |
| WO | 2010102307 A1 | 9/2010 |
| WO | 2010146581 A1 | 12/2010 |
| WO | 2011013556 A1 | 2/2011 |
| WO | 2011066961 A1 | 6/2011 |
| WO | 2011082319 A1 | 7/2011 |
| WO | 2011095352 A1 | 8/2011 |
| WO | 2011106426 A1 | 9/2011 |
| WO | 2011110316 A1 | 9/2011 |
| WO | 2011135556 A1 | 11/2011 |
| WO | 2012052982 A1 | 4/2012 |
| WO | 2012064726 A1 | 5/2012 |
| WO | 2012081020 A1 | 6/2012 |
| WO | 2012110619 A1 | 8/2012 |
| WO | 2012120490 A2 | 9/2012 |
| WO | 2012156924 A1 | 11/2012 |
| WO | 2013016435 A1 | 1/2013 |
| WO | 2013072777 A2 | 5/2013 |
| WO | 2013105099 A2 | 7/2013 |
| WO | 2013109756 A2 | 7/2013 |
| WO | 2013187927 A1 | 12/2013 |
| WO | 2014047650 A1 | 3/2014 |
| WO | 2014081892 A1 | 5/2014 |
| WO | 2014139845 A1 | 9/2014 |
| WO | 2014169266 A1 | 10/2014 |
| WO | 2014178198 A1 | 11/2014 |
| WO | 2015061365 A1 | 4/2015 |
| WO | 2015103547 A1 | 7/2015 |
| WO | 2015134625 A1 | 9/2015 |
| WO | 2015179324 A2 | 11/2015 |
| WO | 2015189354 A1 | 12/2015 |
| WO | 2016010995 A1 | 1/2016 |
| WO | 2016089451 A1 | 6/2016 |
| WO | 2017089424 A1 | 6/2017 |
| WO | WO 2017/090473 A1 | 6/2017 |
| WO | WO 2017/103686 A2 | 6/2017 |
| WO | WO 2017/161204 A1 | 9/2017 |
| WO | WO 2020/039082 A1 | 2/2020 |
| WO | WO 2021/113302 A1 | 6/2021 |

\* cited by examiner

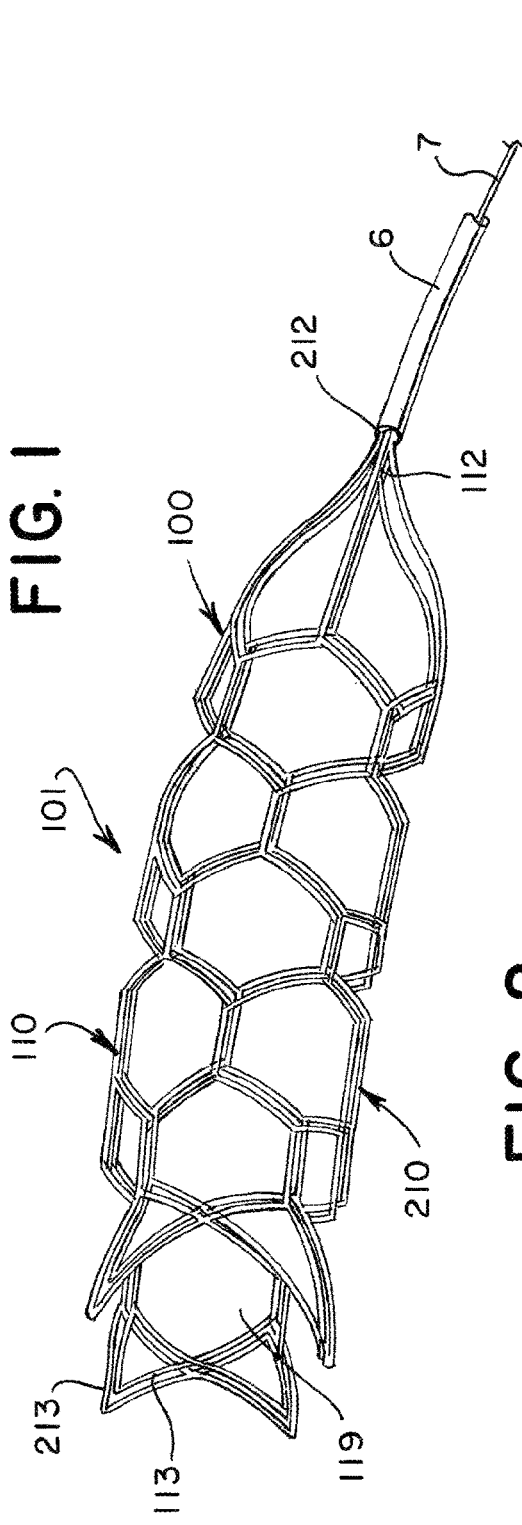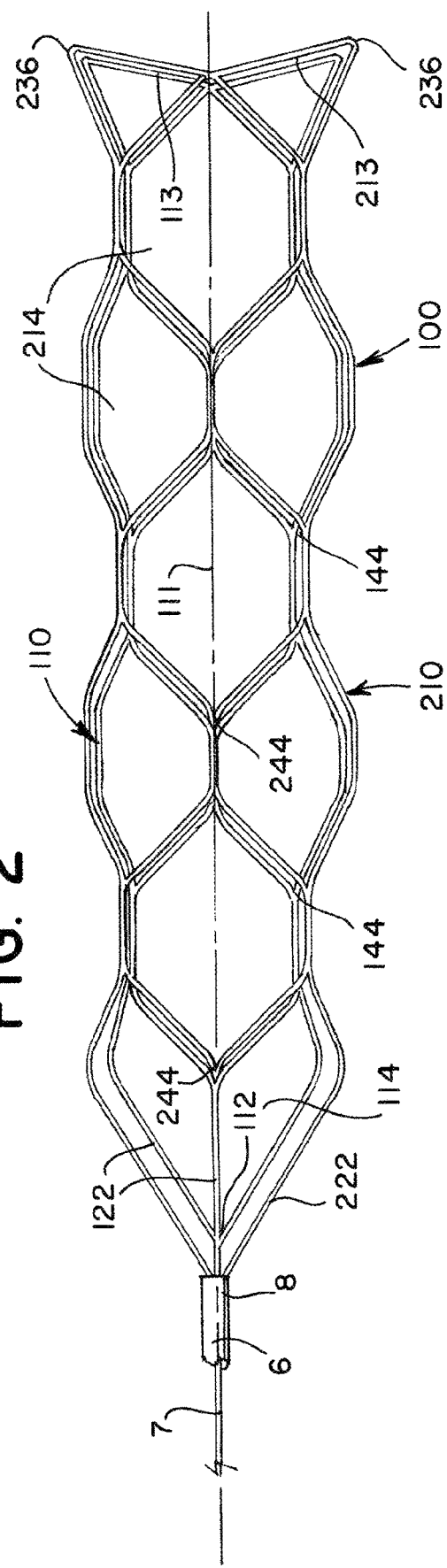

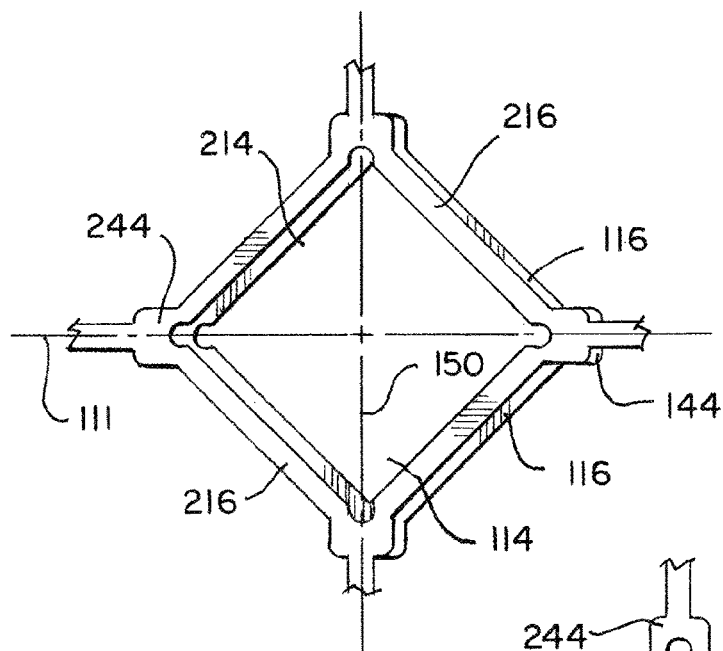
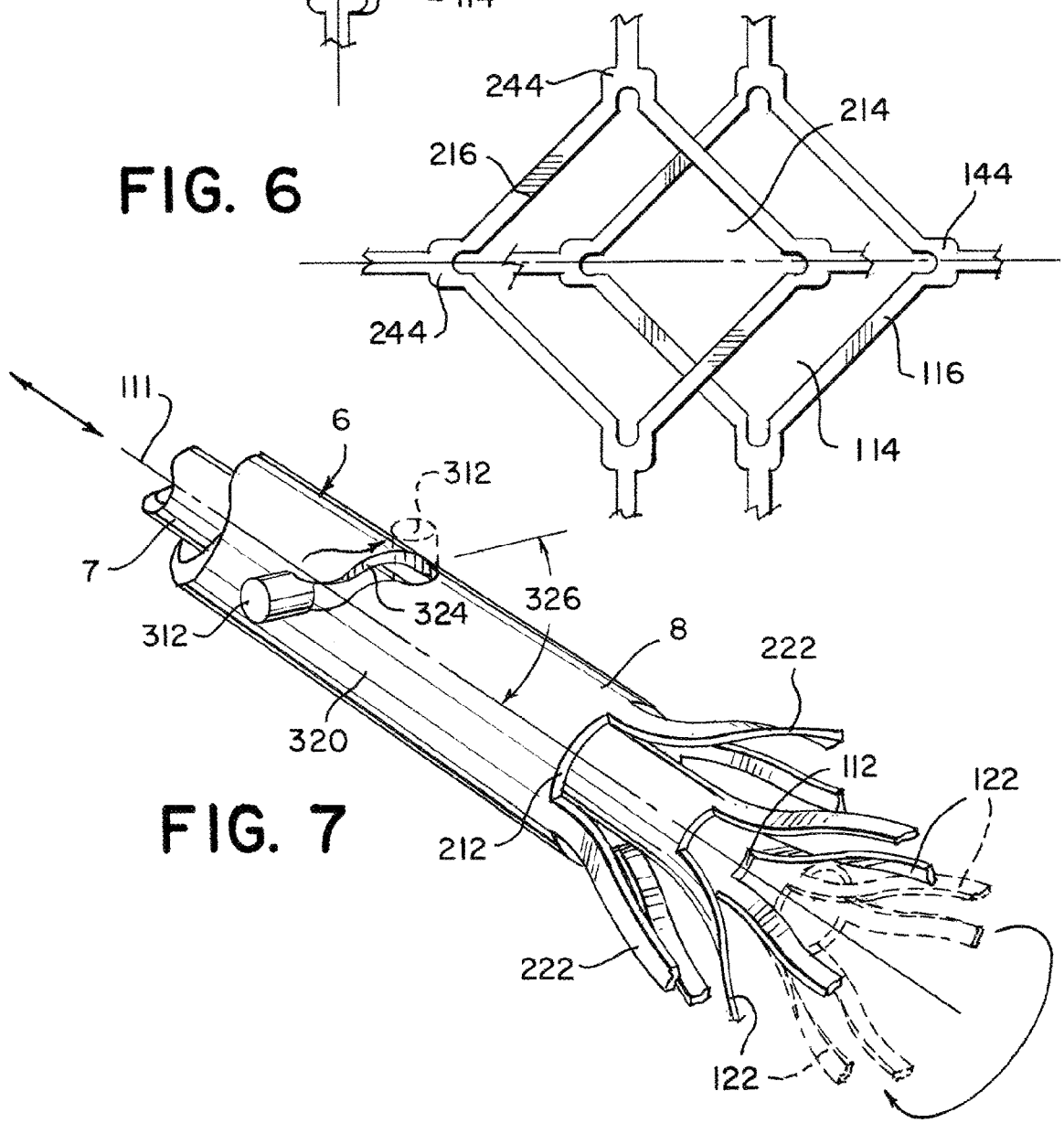

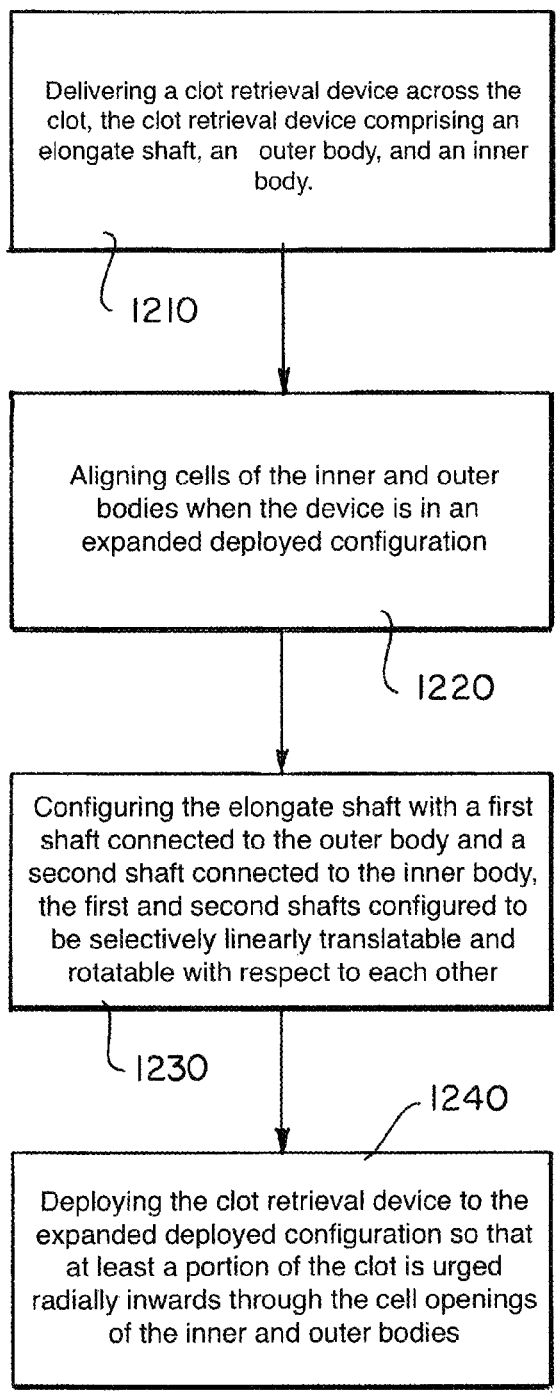
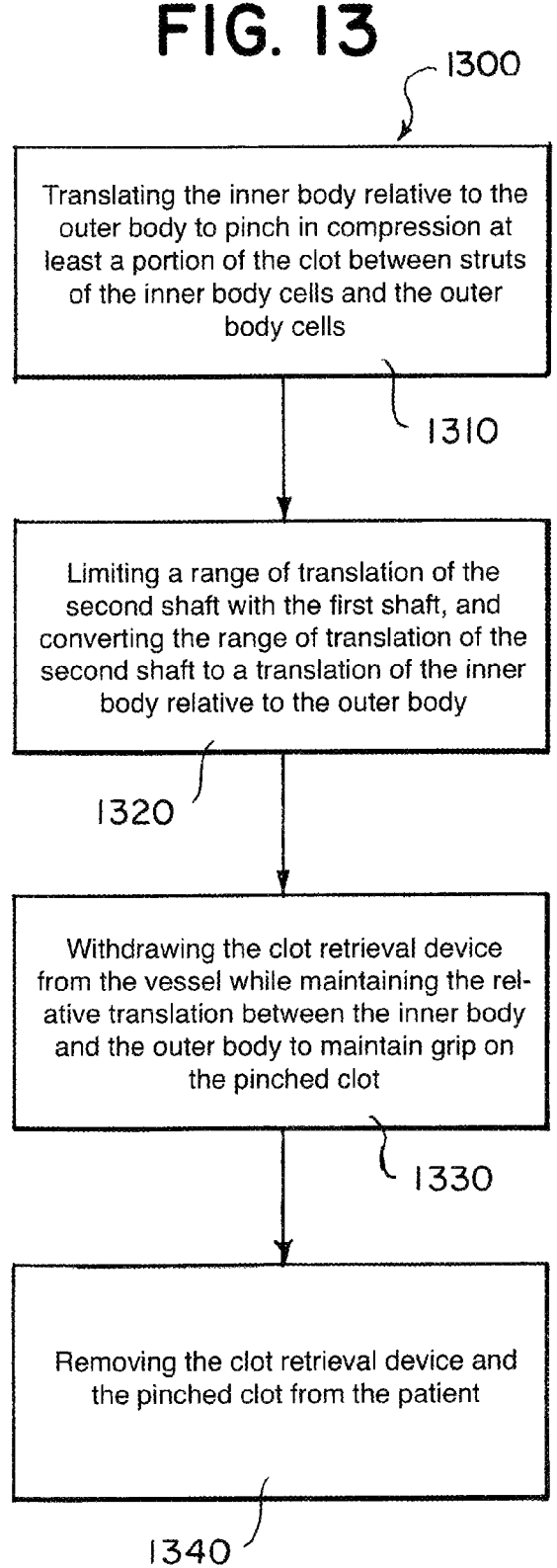

ROTATING FRAME THROMBECTOMY DEVICE

FIELD OF THE INVENTION

The present disclosure generally relates to devices and methods for removing acute blockages from blood vessels during intravascular medical treatments. More specifically, the present disclosure relates to a clot retrieval device for removing a clot from a blood vessel.

BACKGROUND

This disclosure relates to devices and methods of removing acute blockages from blood vessels. Acute obstructions may include a clot, misplaced devices, migrated devices, large emboli, and the like. Thromboembolism occurs when part or all of a thrombus breaks away from the blood vessel wall. This clot (now called an embolus) is then carried in the direction of blood flow, which can result in many complications. An ischemic stroke may result if the clot lodges in the cerebral vasculature. A pulmonary embolism may result if the clot originates in the venous system or in the right side of the heart and lodges in a pulmonary artery or branch thereof. Clots may also develop and block vessels locally without being released in the form of an embolus, and this mechanism is common in the formation of coronary blockages. The devices and methods herein are particularly suited to removing clots from cerebral arteries in patients suffering acute ischemic stroke (AIS), from pulmonary arteries in patients suffering from pulmonary embolism (PE), from coronary native or graft vessels in patients suffering from myocardial infarction (MI), and from other peripheral arterial and venous vessels in which clot is causing an occlusion.

There are a number of access challenges that can make it difficult to deliver devices to a target site. In cases where access involves navigating the aortic arch (such as coronary or cerebral blockages) the configuration of the arch in some patients makes it difficult to position a guide catheter. The tortuosity challenge is even more severe in the arteries approaching the brain. It is not unusual at the distal end of the internal carotid artery that the device will have to navigate a vessel segment with several extreme bends in quick succession over only a few centimeters of travel. In the case of pulmonary embolisms, access may be gained through the venous system and then through the right atrium and ventricle of the heart. The right ventricular outflow tract and pulmonary arteries are delicate vessels that can easily be damaged by inflexible or high-profile devices. For these reasons it is desirable that a clot retrieval device be compatible with as low profile and flexible access and support catheters as possible.

The vasculature in the area in which the clot may be lodged is often fragile and delicate. For example, neurovascular vessels are more fragile than similarly sized vessels in other parts of the body and are located in a soft tissue bed. Excessive tensile forces applied on these vessels can result in perforations and hemorrhage. Pulmonary vessels are larger than those of the cerebral vasculature, but are also delicate in nature, particularly more distal vessels.

Stent-like clot retrieval devices are being increasingly used to remove a clot from cerebral vessels of acute stroke patients. These devices often rely on a pinning mechanism to grab the clot by trapping it between the self-expanding stent-like body and the vessel wall. This approach has a number of disadvantages.

A stent-like clot retriever depends on its outward radial force to retain its grip on the clot during retraction. This compressive force will tend to dehydrate the clot, which in turn can increase its coefficient of friction, making it more difficult to dislodge and remove from the vessel. If the radial force is too low the stent-like clot retriever will lose its grip on the clot, but if the radial force is too high the stent-like clot retriever may damage the vessel wall and require too much force to withdraw. Therefore stent-like clot retrievers that have sufficient radial force to deal with all clot types may cause vessel trauma and serious patient injury, and stent-like clot retrievers that have appropriate radial force to remain atraumatic may not be able to effectively handle all clot types in diverse thrombectomy situations. Pinning the clot between the stent-like clot retriever and the vessel wall also results in high shear forces against the side of the clot as it is removed, potentially releasing fragments of the clot. If these fragments are not retained by the device, they may migrate leading to further blockages in the distal vasculature.

Certain conventional stent-like clot retriever designs also do not retain their expanded shape very well when placed in tension in vessel bends, due to the manner in which their strut elements are connected to one another which results in the struts being placed in tension during retraction. This tension is due to friction between the device and the blood vessel and is increased if an additional load is applied load such as the resistance provided by a clot. This can result in a loss of grip on the clot as the stent-like clot retriever is withdrawn proximally around a bend in a tortuous vessel, with the potential for the captured clot to escape. In a bend, the struts on the outside of the bend are placed in higher tension than those on the inside. In order to attain the lowest possible energy state, the outside surface of the clot retrieval device moves towards the inside surface of the bend, which reduces the tension in the struts, but also reduces the expanded diameter of the device.

Furthermore, when attempting to remove long clots, a conventional device that is shorter than the clot is unlikely to be able to restore flow through the occluded area upon deployment. As a result, the pressure gradient across the clot remains a significant impediment to its removal. Simply making such a device longer would likely render it difficult to track through tortuous anatomies and can be traumatic to the vasculature, taking more force to withdraw and potentially getting the device stuck, requiring surgery to remove.

The effectiveness of a given device is also important as, for many reasons, it is often necessary for a physician to make multiple passes in order to fully remove an obstruction. Each time a clot retrieval device is withdrawn the access to the target site is lost. Thus, it can be necessary to re-advance a guidewire and microcatheter to access and re-cross the clot, and then remove the guidewire and advance the clot retrieval device through the microcatheter. Navigating the guidewire and microcatheter to the clot can take a considerable amount of time especially if the vessels are tortuous. This additional time and device manipulation add to the risks of complication to which the patient is exposed, highlighting the importance of effective and efficient devices.

In seeking procedural efficiency in this environment, devices with multiple bodies have often been preferred. Such devices can have an outer body capable of scaffolding a target vessel and an inner body for embedding and capturing a clot. These devices can perform well in engaging with and dislodging a clot but having a larger and often stiffer network of struts can potentially make it more difficult to retract the device and partially or fully collapse to re-sheath it within an outer catheter. Since these devices are designed so the clot is typically required to migrate through the outer member, the outer member can have a less firm grip on peripheral regions of a clot. The larger expanded shape of the outer body can result in the outer body struts impinging on or deflecting those of the inner body as the device is partially or fully collapsed during retraction.

The challenges described above need to be overcome for any device to provide a high level of success in removing a clot, restoring flow and facilitating good patient outcomes. The present designs are aimed at providing an improved clot retrieval device to address the above-stated deficiencies.

SUMMARY

The disclosed designs for a clot retrieval device resolve these questions by providing a dual-layer device in which the inner and outer members work in unison to capture the entirety of a clot along the full length of the device. The designs can feature a deployed configuration where both the inner and outer members have large cell openings which are aligned to allow the applied radial force to migrate a clot through the openings when the device is expanded. One of the members can then be translated relative to the other so that the aligned cell openings close down, compressively pinching a clot between the opposite edges of the cells of the inner and outer members. This action increases the security of the device's grip on a clot during all phases of retrieval, allowing safer and more efficient flow restoration.

The device can have a collapsed delivery configuration when constrained within an outer catheter and an expanded clot engaging deployed configuration when deployed at a target site. The device can have an elongate shaft for independent manipulation. The shaft can connect to a framework of struts forming an expandable member extending distally from the shaft. The elongate shaft can feature a first shaft and a second shaft translatable and/or rotatable with respect to the first shaft. The shafts can be used to control and activate functions of the expandable member by a user during a procedure.

The expandable member can have a dual layer construction with an inner body connected to the second shaft and an outer body connected to the first shaft. The bodies can enclose a substantially tubular inner lumen and longitudinal axis extending therethrough. The properties of the inner and outer bodies may be tailored independently of each other. The outer body can be coaxial with the inner body or can be radially offset. The inner body can be arranged substantially within the lumen of the outer body.

The inner body can have a plurality of cells and be translatable with respect to the outer body about the longitudinal axis. The outer body can also have a plurality of closed cells and have a radial size greater than that of the inner body when in the expanded deployed configuration and can be configured to appose with and support the walls of a target vessel. The outer body can also be translatable with respect to the inner body about the longitudinal axis. The translation can transition the device between the expanded deployed configuration and a clot pinching configuration.

The cells of the inner and outer bodies of the expandable member can be approximately equal in size, or they can be sized differently so there is some overlap between the boundaries of the cells. When deployed to the expanded configuration across a clot at the target site, the struts of the cells of the inner and outer bodies can engage with and imbed in the clot through exerting a radial force to compress it against the walls of the vessel. The cells of the inner and outer bodies can be aligned so that this compression urges at least portions of the clot to migrate radially inward through the cells and towards the inner tubular lumen. The radial force exerted by the outer member can be greater than or less than the radial force exerted by the inner member. In other examples the radial force of the inner and outer members can be approximately equal.

The cells of the inner body and the cells of the outer body can become offset when the user translates the inner or outer body with respect to the other, such as using the first and second shafts. The translation can be linear along the longitudinal axis, rotation about the axis, or a combination of these. The translation can compress and pinch a clot between the struts of the offset cells of the bodies as the relative motion transitions the device from the expanded deployed configuration to the clot pinching configuration. This pinch in the cells constricts portions of a clot so that it is gripped securely as the device is retracted from the target site. The relative translation between the inner body and outer body can be maintained as the clot is withdrawn so that the device remains in the clot pinching configuration and the grip is not lost.

The translation of the inner and outer bodies for the clot pinching configuration can be actuated through the first and second shafts of the device. For example, the first shaft can have an elongate tubular body having an internal lumen and a slot through the wall thickness approximate its distal end. The second shaft can be a cylindrical member disposed within the lumen of the first shaft, so the two shafts are movable with respect to each other. An indexing pin can extend radially outward from the outer surface of the second shaft so that it is configured to engage and move within the confines of the slot in the first shaft. The indexing pin and slot can be sized so the circumferential rotation and/or axial motion of the pin (and thus the inner shaft and inner body) is guided through the length of the slot. The orientation of the slot, for instance, can parallel the longitudinal axis or can be oriented such that the axis of the slot forms an angle with the longitudinal axis of the device. If a user then pushed or pulled the elongate body of the inner shaft along the axis of the shaft, the indexing pin can undergo motion along the slot axis, allowing rotation and translation of the inner shaft and inner body relative to the outer shaft and outer body. This motion can offset the cells of the inner and outer bodies to pinch and securely grip the clot. The process can also be reversed to transition the device from the clot pinching configuration back to the expanded deployed configuration.

In another example, the inner body can have inner support arms joined to the second shaft and the outer body can have outer support arms joined to the first shaft. These support arms can be formed at an angle to twist about the longitudinal axis. The tangential forces on the inner or outer support arms can then affect a twist on the inner body and/or outer body of the device with respect to each other when an outer or access catheter is advanced upon the device. This relative twist can cause the translation necessary to pinch and securely grip the clot.

In another example, a device for treating a clot or occlusion in a body vessel can have a tubular inner lumen configured about a longitudinal axis. The device can have an inner body with a constrained delivery configuration, an expanded deployed configuration, and a plurality of struts forming a porous inner clot scaffolding section. An outer body can be disposed around the inner body and share a constrained delivery configuration and an expanded deployed configuration. The outer body can also be porous with an interconnected plurality of struts forming an outer clot scaffolding section. Extending proximal of the inner and outer bodies can be an elongate shaft allowing a user to control and manipulate the device.

The struts of the scaffolding sections of the inner body and outer body can form rings of open or closed cells. The cells can be approximately equal in size or can be of different sizes. The cells of the inner body can align with the cells of the outer body when the device is delivered from the constrained delivery configuration to expand to the deployed configuration at a target site. The expansion of the scaffolding struts can exert an outward radial force on the clot or occlusion, embedding the struts of the scaffolding sections and prompting portions of the clot to migrate and protrude radially inwards through the openings in the aligned cells and towards the inner tubular lumen.

The inner and outer bodies can be translatable relative to one another about the longitudinal axis. This translation can be activated by a user through manipulation of the elongate shaft. The shaft can have a first shaft attached to the outer body enclosing a second shaft connected to the inner body, such that the first and second shafts are translatable with respect each other. In this way, when a user translates and/or rotates the inner second shaft while holding the outer first shaft steady, the inner body translates and/or rotates with respect to the outer body. Similarly, when a user translates and/or rotates the first shaft while maintaining the position of the second shaft, the outer body translates and/or rotates with respect to the inner body. Depending on the construction of the first and second shafts, the relative translations can be linear motion, rotation about the longitudinal axis, or a combination of the two. The translations of the bodies can cause the inner and outer body cells through which the clot is protruding to become offset, thus compressing the clot between opposing edges of the respective cells.

A method for utilizing the disclosed devices to treat a patient with a clot occluding a vessel can have the step of delivering a clot retrieval device across the clot. The device can have a collapsed delivery configuration and an expanded deployed configuration, an elongate shaft for controlling the device, and an expandable element distal of the elongate shaft. The collapsed delivery configuration allows the clot retrieval device to be delivered through a catheter with a relatively small bore, such as a microcatheter, before expanding at the target site when the catheter is withdrawn.

The expandable element can have an inner body comprising a plurality of cells and an outer body comprising plurality of cells and expandable in the deployed condition to a greater radial size than the inner body. The inner body and outer body can be configured to translate relative to one another about the longitudinal axis between the deployed configuration and a clot pinching configuration.

The elongate shaft can have a first shaft connected to the outer body and a second shaft connected to the inner body. Translation of the outer and inner bodies can be accomplished by, for example, configuring the first shaft and second shaft to be selectively movable with respect to the each other. The method can then include the step of selectively imparting the motion on the outer body relative to the inner body with the first shaft or utilizing the second shaft to selectively impart the motion on the inner body relative to the outer body. The motion can be linear, curvilinear, rotational, a combination of these, or another suitable profile.

Another step can involve limiting the range of translation of the first and second shafts relative to each other. A limiting function can help prevent a user from translating the inner and outer bodies beyond a design limit, where the growing offset of the cells of the bodies can loosen the grip on or shear the clot. A limit can be implemented by using a slot, sleeve, cam/follower, or other suitable arrangement as a physical stop to block further translation of the shafts.

A further step can involve deploying the clot retrieval device to the expanded deployed configuration so that the cells of the inner body are aligned and exposed with the cells of the outer body. When expanded, both the inner and outer bodes can exert and outward radial force on the clot, pinning the clot against the vessel wall and urging at least a portion of the clot radially inward through the openings in the cells of the inner and outer bodies. When portions of the clot have protruded through the cell openings, the user can translate one of the inner or outer bodies relative to the other, transitioning the device from the expanded deployed configuration to pinch the clot between the struts of the inner and outer body cells. The pinched clot is held firmly in compression between the cells, allowing the clot retrieval device to be withdrawn from the vessel while the grip is maintained by preserving the relative translation between the inner and outer bodies. The clot retrieval device and pinched clot can then be retrieved from the patient, either independently or by withdrawing the device and clot into an outer or intermediate catheter.

In many cases, after retrieving some or all of the occlusive clot, contrast media can be injected through the outer catheter to allow a more thorough assessment of the degree to which the vessel is patent. Additional passes with the clot retrieval device can be made if an obstruction remains in the vessel. Any remaining devices can then be removed from the patient once adequate recanalization of the target vessel is observed. The devices of the present disclosure provide a means to minimize the number of catheter advancements required to treat a patient, thereby reducing the likelihood of vessel damage and the associated risk of vessel dissection in cases where multiple passes are required.

Other aspects and features of the present disclosure will become apparent to those of ordinary skill in the art, upon reviewing the following detailed description in conjunction with the accompanying figures.

BRIEF DESCRIPTION OF THE DRAWINGS

The above and further aspects of this invention are further discussed with reference to the following description in conjunction with the accompanying drawings, where like reference numbers indicate elements which are functionally similar or identical. The drawings are not necessarily to scale, emphasis instead being placed upon illustrating principles of the invention. The figures depict one or more implementations of the inventive devices, by way of example only, not by way of limitation.

FIG. 1 is an isometric view of a clot retrieval device according to aspects of the present invention;

FIG. 2 shows a side view of another clot retrieval device according to aspects of the present invention;

FIG. 5 demonstrates the alignment of the cells of the inner and outer bodies parallel to the axis of the clot retrieval device in the expanded deployed configuration according to aspects of the present invention;

FIG. 6 shows an example of the orientation of the cells of the device from FIG. 5 in the clot pinching configuration after an applied linear translation of the cells along the device axis according to aspects of the present invention;

FIG. 7 is another example of a possible activation mechanism for the clot pinching orientation using a first shaft and a second shaft according to aspects of the present invention;

FIGS. 12-13 are flow diagrams outlining a method of use for a clot retrieval device according to aspects of the present invention.

DETAILED DESCRIPTION

Figure 3:
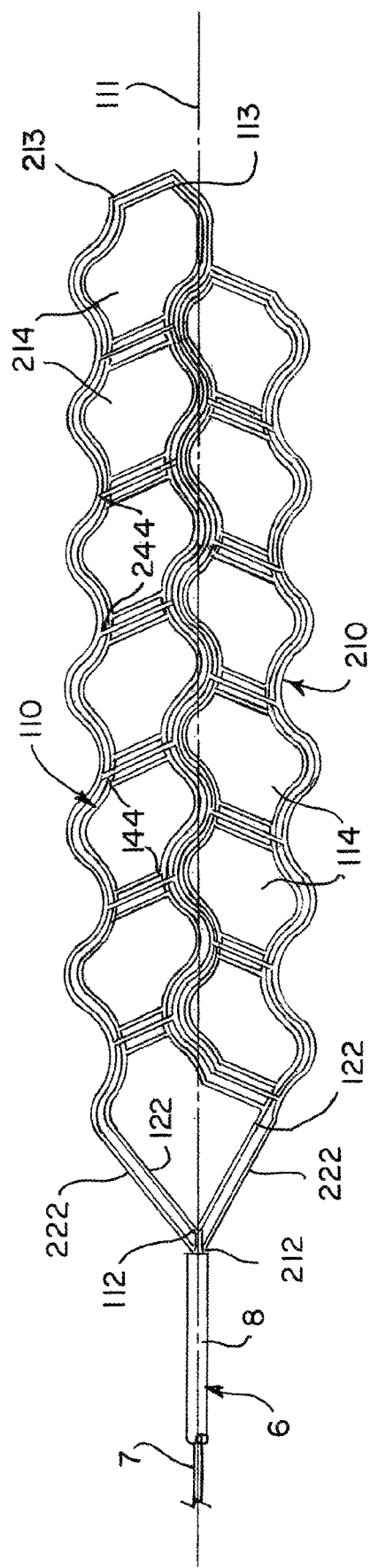
FIG. 3 illustrates a further example of a clot retrieval device according to aspects of the present invention.

The objective of the disclosed designs is to create a clot retrieval device capable of providing more effective and efficient removal of clots of a wide degree of composition in the vasculature while maintaining a high level of deliverability and flexibility during procedures. The designs can have an outer expandable body within which runs an inner expandable body. The disclosed devices share a common theme of dual layer construction where the outer and inner bodies have large cell openings where a radial force allows portions of the clot to migrate into the openings. One of the outer or inner members is then translated with respect to the other body so that the previously-aligned cell openings are closed down, pinching a portion or portions of the clot inside. These pinching designs increase the grip security of the clot retrieval device.

Both the inner and outer expandable members are desirably made from a material capable of recovering its shape automatically once released from a highly strained delivery configuration. The material can be in many forms such as wire, strip, sheet, or tube. A suitable manufacturing process can be to laser cut a Nitinol tube and then heat set and electropolish the resultant structure to create a framework of struts and connecting elements. A range of designs are envisaged for each of these elements as described, and it is intended that any of these elements can be used in conjunction with any other element, although to avoid repetition they are not shown in every possible combination.

Specific examples of the present invention are now described in detail with reference to the Figures. While the description is in many cases in the context of mechanical thrombectomy treatments, the designs may be adapted for other procedures and in other body passageways as well.

Accessing the various vessels within the vascular to reach a clot, whether they are coronary, pulmonary, or cerebral, involves well-known procedural steps and the use of a number of conventional, commercially available accessory products. These products, such as angiographic materials, rotating hemostasis valves, delivery access catheters, and guidewires are widely used in laboratory and medical procedures. When these or similar products are employed in conjunction with the disclosure of this invention in the description below, their function and exact constitution are not described in detail.

Referring to FIG. 1, a clot retrieval device 100 can have an elongate shaft 6 and an expandable member 101 configured at the distal end of the elongate shaft. The expandable member 101 can have an inner body 110 and an outer body 210 expandable from a collapsed or constrained delivery configuration to an expanded deployed configuration at the target site of a vessel occlusion. The delivery method can be through, for example, a microcatheter or other outer catheter depending on the access requirements of the target location. The occlusion can be a thrombus (blood clot), atherosclerotic plaque, or some other blockage impeding blood flow in the vessel.

The outer body 210 can be of a generally tubular shape extending from a proximal end 212 connection to an elongate shaft 6 and a distal end 213. The inner body 110 can also have a substantially tubular profile and extend through the interior of the outer body 210. The inner body 110 can also be connected to the elongate shaft but need not share a connection with the outer body 210. In other words, both bodies can be fixedly connected to the shaft but may not necessarily share the same connection point at the proximal end 112 of the inner body. Certain shaft designs can then allow the inner and outer bodies 110, 210 to be selectively translatable relative to each other so as to be capable of pinching and capturing portions of a clot or occlusion. This clot pinching configuration can be activated by, for example, a rotation or linear translation of the inner body 110 relative to the outer body 210. The pinch facilitates removal of the clot by increasing the grip of the device on the clot, particularly in the case of fibrin rich clots. The pinch may also elongate the clot, thereby reducing the dislodgement force by pulling the clot away from the vessel wall during the dislodgement process. Retention of the clot during can be improved during retraction to the microcatheter or outer catheter by controlling the proximal end of the clot and preventing it from snagging on a side branch vessel.

The distal end 213 of the outer body 210 and the distal end 113 of the inner body 110 can form an annular profile around the axis 111 of the expandable member 101 to define an inner lumen 119 for the device 100. The distal end 213 of the outer body 210 can be planar with the distal end 113 of the inner member 110 or can form another shape in a largely atraumatic contour so as to avoid vessel trauma when deployed and expanded at a target site. In some instances, a flared or contoured end as shown can prove advantageous for situations where angled struts can provide a greater radial force or distal apices 236 on the final ring of cells can be used to help dislodge obstinate clots. The distal apices 236 can be offset from the longitudinal axis 111 of the device 100 and can be close to the cylindrical plane defined by the outer body 210 when expanded.

The inner and outer bodies 110, 210 are preferably made of a super-elastic or pseudo-elastic material such as Nitinol or other such alloy with a high recoverable strain. Some of all of the elongate shaft 6 can be a tapered wire, or may be made of stainless steel, MP35N, Nitinol, or other material having a suitably high modulus and tensile strength. An advantage of using self-expanding bodies with these materials is that because of the volumetric properties and stiffness of a target clot, resistance can cause the device 100 to initially expand to only a fraction of its freely expanded diameter when deployed across the clot. This gives the outer body 210 the capacity to further expand to a larger diameter while being retracted so that it can remain in contact with vessel walls as it is retracted into progressively larger and more proximal vessels.

Shaft 6 and device 100 can also have indicator bands or markers to indicate to the user when the distal end of the device is approaching the end of the microcatheter during insertion or mark the terminal ends of the device during a procedure. These indicator bands can be formed by printing, removing, or masking areas of the shaft for coating, or a radiopaque element visible under fluoroscopy, so that they are visually differentiated from the remainder of the shaft.

The shaft 6 may be coated with a material or have a polymeric jacket to reduce friction and thrombogenicity. The coating or jacket may consist of a polymer, a low friction lubricant such as silicon, or a hydrophilic/hydrophobic coating. This coating can also be applied to some or all of the outer body 210 and inner body 110.

A dual-layer, multi-diameter device 100 as shown in various figures throughout this disclosure has several advantages. Both the outer body 210 and the inner body 110 are self-expanding stent-like structures, with the outer diameter of the inner body approximately equal to the inner diameter of the outer body in the freely expanded state. Thus, when the outer body 210 is constrained within a vessel and/or clot, the inner body 110 will be itself constrained by the outer body. In one example the outer diameter of the inner body 110 is within 20% of the inner diameter of the outer body 210 in their freely expanded states. In a more preferred example, the outer diameter of the inner body 110 is within 10% of the inner diameter of the outer body 210 in their freely expanded states. In the most preferred example, the outer diameter of the inner body 110 is equal to or slightly larger than the inner diameter of the outer body 210 in their freely expanded states if the device were to be disassembled such that the inner body was not constrained within the outer body.

The radial size of the outer body 210 can allow it to remain in contact with and appose the vessel walls as well as protecting against distal migration of the clot as the device is retracted proximally into progressively larger diameter vessels. Apposition with the vessel walls can also reduce the axial force necessary to initially dislodge a clot from the vessel.

A side view of a compound device 100 with dual inner and outer expandable bodies 110, 210 similar to that of FIG. 1 is illustrated in FIG. 2. The inner body 110 and outer body 210 can both be monolithic structures, where the outer body is configured to substantially encompass the inner body within it. The cells 114 of the inner body 110 and the cells 214 of the outer body 210 serve as inlets for the clot and allow the device, when retracted, to apply a force to the clot in a direction substantially parallel to the direction in which the clot is to be pulled from the vessel (i.e. substantially parallel to the longitudinal axis 111). This means that any outward radial force applied to the vasculature by the outer body 210 can be kept to a minimum. By configuring the outer body 210 so as to encourage a clot to traverse to the inner lumen 119 the device can more effectively disengage clot from the wall of the vessel. The inner body 110 and outer body 210 can also have open distal ends 113, 213, or can be configured with a fragment protection element (not shown) to protect against the distal migration of clot fragments or other debris during a procedure.

The cells 114 of the inner body 110 and the cells 214 of the outer body 210 can have various shapes. FIG. 2 shows cells with a largely hexagonal shape but can be some other polygon. These cells of the inner body and outer body can allow the device to accommodate minor length differentials through stretching without the application of significant tensile or compressive forces to the joints. Length differentials can occur when, for example, the device is expanded, collapsed or deployed in a small vessel. A hexagonal arrangement of the struts of the inner body cells 114 and outer body cells 214 does allow the cells to lengthen and shorten enough so that the lengths of the inner body 110 and outer body 210 can be substantially the same when loaded in a microcatheter and when freely expanded at the target site. However, the shape of the cells can have sufficient structural rigidity so the device 100 can be advanced or retracted without excessively lengthening or shortening the inner body 110 and outer body 210.

The shape for the cells 114, 214 can be chosen to not significantly impair a clot's ability to pass at least partially into the interior of the device 100. In many cases, the cells can be closed as illustrated with the apices of inner body cells 114 joined together with adjacent cells at inner junctions 144 and outer body cells 214 joined at outer junctions 244. In another example, there can be a combination of open and closed cells, where open cells have a ring of struts that are discontinuous from an axially adjacent ring of cells.

The inner body 110 and outer body 210 can be configured to develop different radial forces upon expansion to the deployed configuration. This can be accomplished through multiple methods, such as differing geometries, materials, or through heat setting with different residual strains. In one example, the outer body 210 can have limited radial force so as not to cause vessel trauma and the inner body 110 can have a higher radial force so a strong opening force can create a lumen through at least a portion of the clot to restore blood flow on deployment. Some amounts of restricted blood flow through the lumen can ensure that the pressure applied to blood vessels immediately after flow restoration is lower than normal and thereby reducing the risk of bleeding in the vascular bed. Full perfusion can be subsequently restored by removing the device and the captured clot. In other examples, the radial force of the outer body 210 and radial force of the inner body 110 can be substantially equal, or the outer body can have a greater radial force so as to both pinch and twist portions of the clot when the bodies are translated.

Device shaft 6 can be subdivided into two separate shafts, a first shaft 8 and a second shaft 7, coincident with each other and the longitudinal axis 111 of the device 100. Proximally, the outer body 210 of the device can have support arms 222 joined at a proximal junction with first shaft 8 and flare radially in a conical fashion to the full diameter of the body. The support arms 222 may have a tapered profile as shown to ensure a gradual stiffness transition from the first shaft 8 to the fully tubular profile of the outer body 210 which engages the clot. Support arms 222 can vary in number and location at discreet positions around the longitudinal axis 111 of the device 100 so that there are small or large circumferential gaps between adjacent arms.

The inner body 110 can have inner support arms 122 joining to second shaft 7. Similar to the support arms 222 of the outer body 210, the inner support arms 122 can taper from the tubular portion of the inner body to shaft 7 and can be parallel to, or at an angle to, or be twisted about the longitudinal axis 111. If formed with a twist about the axis, the support arms 122 can induce a twist on the inner body 110 of the device with respect to outer body 210 when withdrawn into an outer catheter. Alternately, a suitable outer catheter can be advanced upon the device to impinge upon the support arms 122. This rotational twist can be another method of closing the previously aligned cells 114, 214 of the inner and outer bodies to grasp the clot in the clot pinching configuration. Similarly, even if a pinch has already been achieved between the cells of the inner body 110 and outer body 210 through a relative translation, the device can still be withdrawn into an outer catheter if desired, impinging the inner support arms 122 and outer support arms 222 to further pinch a proximal portion of the clot while the cells of the expandable bodies can maintain a secure grip on the clot without interfering.

Support arms 122 can also have bends or crowns which would bias movement away from, or at least not in the same direction as, the clot pinching cells so that the support arms do not shear portions of the clot when the proximal portion of the device is partially constrained by an outer catheter. The bends or crowns can also help to provide a strong grip on the clot for the critical initial step of disengaging the clot from the vessel, enabling the outer body 210 to be configured with a low radial force. Connections of the inner body cells 114 and outer body cells 214 to the support arms 122, 222 can be substantially aligned to align the neutral axis of the inner and outer bodies during bending within the vasculature.

The distal-most portion of the inner body 110 and outer body 210 can be open as illustrated, or alternately have a tapered end which slims down radially in a substantially conical profile to a distal end 213. The tapering and convergence of struts at the end can reduce the pore size of the cell openings between struts to create a fragment capture zone. In a further example, distal apices 236 can be included which are bulged or flared so the distal end 213 of the outer body 210 is rendered atraumatic to the vessels in which it is used. The struts making the bulge or flare might not be parallel to those of the adjacent portions of the outer body 210. The distal end 213 can also be given radiopaque properties to mark the terminal end of the device 100 during a procedure.

Another example of a clot retrieval device 100 having dual layer construction with an inner body 110 and an outer body 210 disposed around a longitudinal axis 111 is shown in FIG. 3. In this example, the cells 114 of the inner body 110 and cells 214 of the outer body 210 can have an irregular shape, whereby the struts have bends or extend in a curvilinear fashion which may not be mirrored axially from one set or ring of cells to the next. In the illustration, rings of cells forming the device can be bounded by sinusoidal edges where they meet at inner body junctions 144 and outer body junctions 244. The sinusoidal edges mean the magnitude (or amplitude) of the radial force peaks and troughs can vary along the length of the device 100. This irregular cell shape can give the device acute angles and higher radial pressures (radial force per surface area) in different regions to aid with imbedding and gripping a clot.

Where portions of a clot contact the device, low surface area and radial force can allow parts of the clot to protrude through the inner body cells 114 and outer body cells 214. For a given level of radial force, the radial pressure of the device can be increased by reducing the number of struts making up the cells or the strut width.

Figure 4:
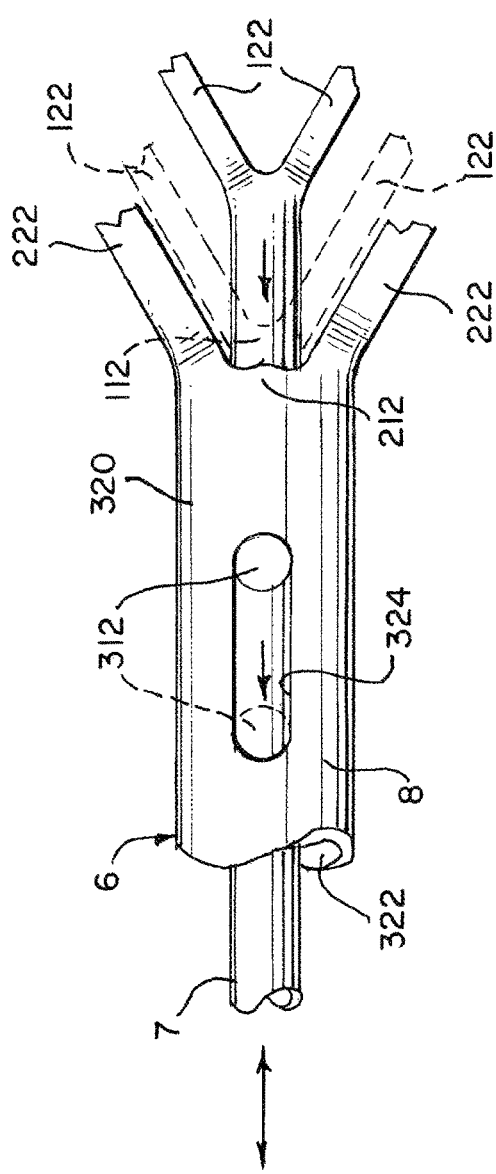
FIG. 4 is an example of a possible activation mechanism for the clot pinching orientation using a first shaft and a second shaft according to aspects of the present invention.

The elongate shaft 6 can be constructed so the inner body 110 and outer body 210 can be manipulated and/or translated independently. The translation can be, for example, a linear translation along an axis, a rotation of one body with respect to the other, or some combination of these. The user can transition the device 100 from having the cells 114 of the inner body 110 and cells 214 of the outer body 210 aligned when in the expanded deployed configuration to being offset in the clot pinching configuration in a number of ways. An example of this change in orientation is demonstrated in FIG. 5 and FIG. 6, where FIG. 5 is indicative of cells which are initially aligned when the device is first deployed within a target clot. As shown in FIG. 4, device shaft 6 can be subdivided into two separate shafts coincident with each other and the longitudinal axis 111 of the device 100. Shaft construction can be of sufficiently stiff materials or combination of materials to allow force transmission from a user at a proximal end external to the patient. First shaft 8 can be connected to the proximal end 212 of the outer body 212 and second shaft 7 can be connected to the proximal end 112 of the inner body 110. First shaft 8 can have a tubular elongate body 320 such that second shaft 7 can reside within the lumen 322 of the first shaft.

The clot pinching configuration of the device 100 can be achieved by a translation of the inner body 110 relative to the outer body 210, or alternately a translation of the outer body 210 relative to the inner body 110. In the example illustrated in FIG. 4, an indexing pin 312 can extend radially from the second shaft 7 and reside in a slot 324 in the elongate body 320 of the first shaft 8. If the axis of slot 324 is arranged parallel to that of the longitudinal axis 111 as shown, then a user can push or pull the one shaft relative to the other to induce a linear translation in the body cells.

When the cells are aligned as in FIG. 5, for example, holding the first shaft 8 steady while pushing the second shaft 7 causes a linear translation along the axis 111 of the inner body 110, closing the cells 114 of the inner body with the protruding clot relative to the cells 214 of the outer body 210. The translation results in a new orientation of the cells 114, 214 as seen in FIG. 6. The angled junctions 144 formed by the struts 116 of the inner body 110 can function as a net during the translation, grasping a protruding portion of the clot and pinning it against the respective junctions 244 formed by the struts 216 of the outer body 210. In an alternative example, holding the second shaft 7 steady while pushing or pulling the first shaft 8 causes a linear translation along the axis 111 of the outer body 210, closing the cells 214 of the outer body with the relative to the cells 114 of the inner body 110, pinning the protruding clot. It can also be envisioned that both the first shaft 8 and second shaft 7 can be translated in opposing directions simultaneously, accomplishing the same function. The terminal ends of the slot 324 can limit the allowable applied translation, preventing accidental shearing or loss of grip on a captured clot. Partial resheathing of the device 100 during retrieval with a microcatheter, intermediate catheter, or other outer sheath can add an additional pinch to the protruding clot (in addition to that between the cells of the inner body and outer body) between the tip of the catheter or sheath and the proximal struts of the inner body 110 and the outer body 210.

Figure 8:
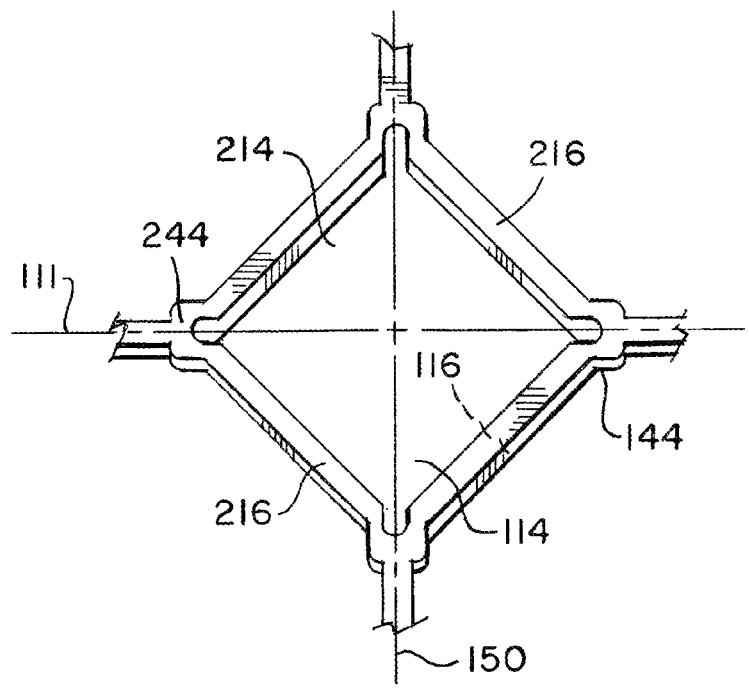
FIG. 8 demonstrates the alignment of the cells of the inner and outer bodies transverse to the axis of the clot retrieval device in the expanded deployed configuration according to aspects of the present invention.
Figure 9:
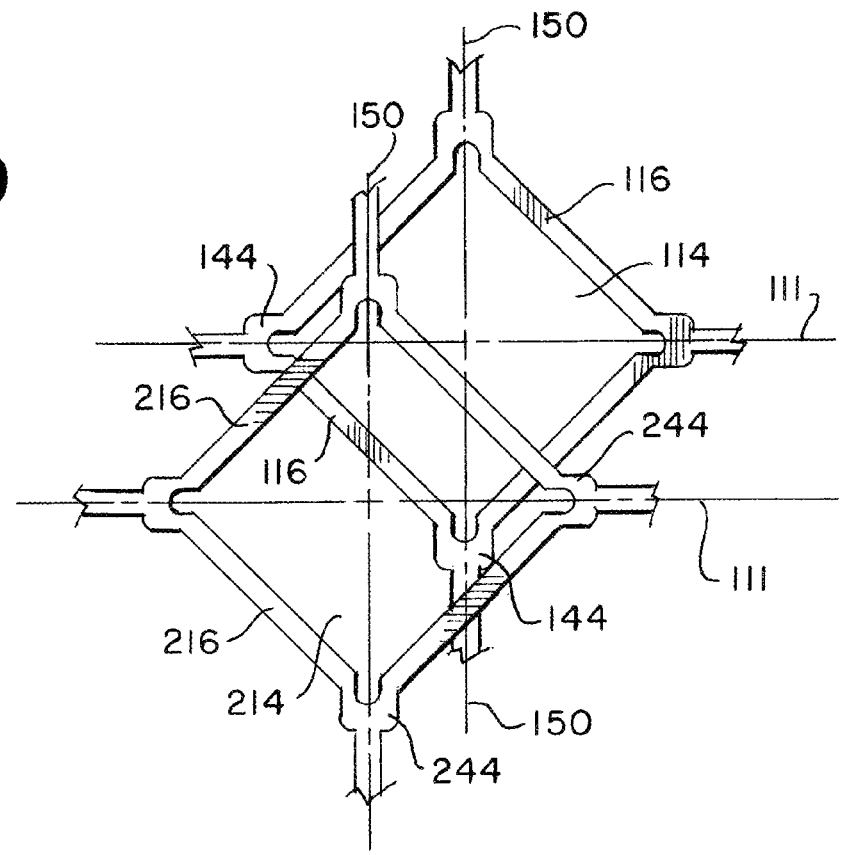
FIG. 9 shows an example of the orientation of the cells of the device from FIG. 8 in the clot pinching configuration after an applied translation and rotation of the cells about the device axis according to aspects of the present invention.

Another example using an indexing pin as a means to control the device 100 transition to the clot pinching configuration is illustrated in FIG. 7. Similar to previous examples, a second shaft 7 can reside in the lumen 322 of a tubular first shaft 8 so that the shafts are translatable and rotatable relative to each other. The indexing pin 312 can extend radially from the second shaft 7 and reside in a slot 324 cut into the elongate body 320 of the first shaft 8 such that the axis of the slot forms an angle 326 relative to the longitudinal axis 111. If the axis of slot 324 is arranged parallel to that of the longitudinal axis 111 (refer to FIG. 4), then a user can push or pull one shaft relative to the other to induce a linear translation in the body cells. However, an angular slot as shown means that a push/pull force on the second shaft 7 relative to the first shaft 8 results in both a linear translation and angular rotation (see arrows in FIG. 7) of the inner body member 110 with respect to the outer body member 210. A single push/pull force from the user is necessary for this activation since the slot 324 guides the necessary travel of the indexing pin 312. This motion transitions from the deployed condition of the inner body cells 114 and outer body cells 214 as shown in FIG. 8 to the clot pinching configuration of the cells offset from axis 111 and axis 150 as shown in FIG. 9.

It can be understood that with this method of activating the clot pinching configuration for the device 100, a more acute angle 326 relative to the longitudinal axis 111 for the slot 324 in the first shaft 8 in a greater relative component of linear translation between the cells 114 of the inner body 110 and cells 214 of the outer body 210. Similarly, if a more obtuse angle 326 would yield a greater relative component of rotation of the bodies about the axis 111.

Figure 10:
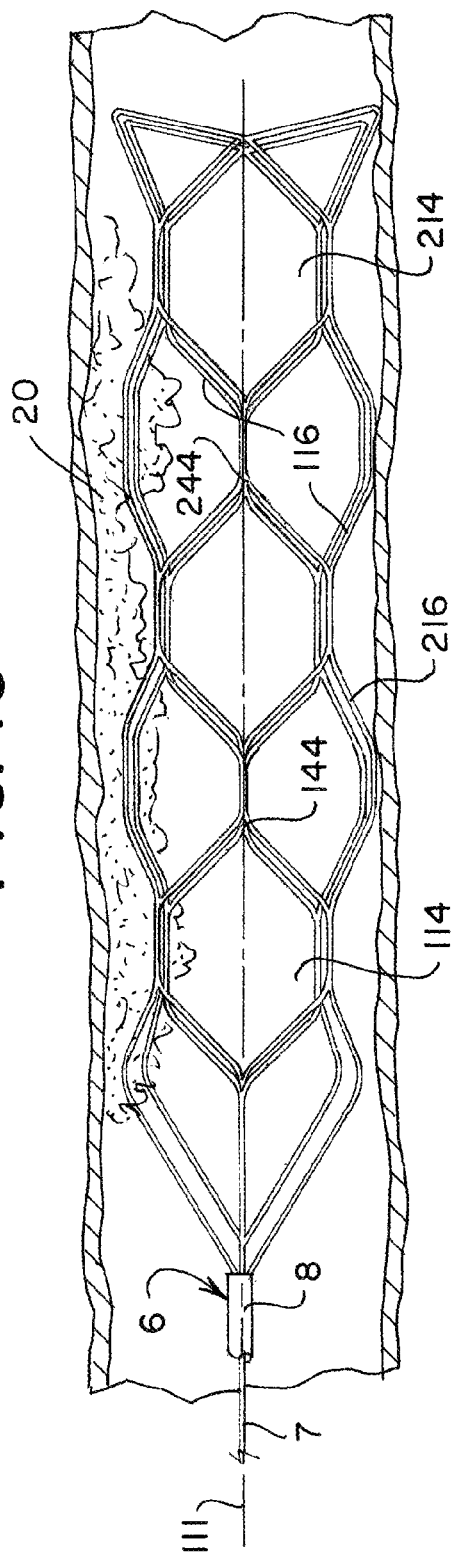
FIG. 10 is a view of the aligned cells of the inner and outer bodies allowing a clot to migrate through the cell openings in the expanded deployed configuration according to aspects of the present invention.
Figure 11:
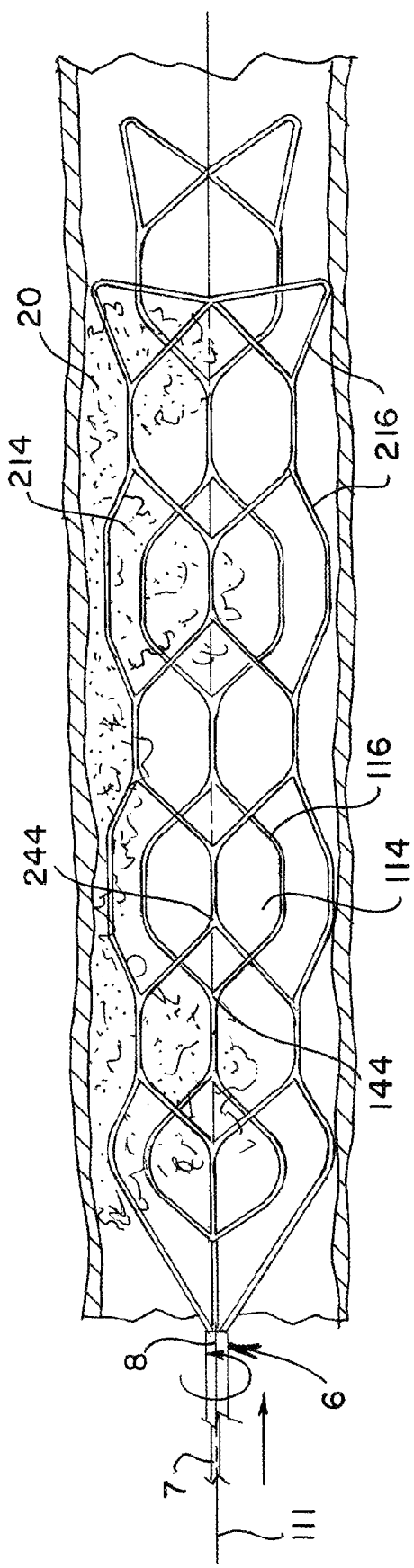
FIG. 11 illustrates the cells of FIG. 10 where the inner body has been rotated about the axis to the clot pinching configuration according to aspects of the present invention.

Broader views of the inner body 110 and outer body 210 of the device 100 in the expanded deployed configuration and after being manipulated to the clot pinching configuration are shown in FIG. 10 and FIG. 11, respectively. The outer body 210 can expand and contact the vessel wall as the microcatheter is retracted during device deployment. The apposition with the wall provides stability to the device 100 and minimizes twisting on deployment between the outer body 210 and the inner body 110 as the device is unsheathed in the vessel. This facilitates uniform deployment and expansion of the device 100 in the obstruction or clot 20 by pinning the clot against the vessel wall. When deployed, the radial force from the expansion of the bodies about axis 111 results in the clot 20 being urged through the openings in the cells 114, 214.

Expansion of the inner body 110 and outer body 210 can cause compression and/or displacement of the clot during the expansion, depending on the level of scaffolding support provided by the struts. When an expandable body provides a high level of scaffolding the clot can be compressed. Alternately, when an expandable body provides an escape path or opening the expanding body urges the clot towards the opening. The clot itself can have many degrees of freedom and can move in a variety of different directions. When the device is sufficiently long, many of the degrees of movement freedom available to the clot are removed. This allows the clot to be retrieved without being excessively compressed. This is advantageous because compression of clot can cause it to dehydrate, which in turn increases the frictional properties and stiffness, which make the clot more difficult to disengage and remove from the vessel. This compression can be avoided if the clot easily migrates inward through the cells or the gaps in the proximal portions of the inner and outer bodies 110, 210 as the bodies expands outward towards the vessel wall.

When the clot pinching configuration is activated by utilizing a relative displacement and/or rotation of the inner body 110 and outer body 210 (arrows in FIG. 11), the struts 116 forming the inner body cells 114 are no longer aligned with the struts 216 forming the outer body cells 214 as shown in FIG. 11. The clot 20 becomes impinged and compressed between the struts forming the cells, allowing the pinch to tightly grip regions of the clot for initial dislodgement and subsequent retrieval from the vessel.

FIG. 12 and FIG. 13 diagram method steps for performing a thrombectomy procedure with such a device. The method steps can be implemented by any of the example devices or suitable alternatives described herein and known to one of ordinary skill in the art. The method can have some or all of the steps described, and in many cases, steps can be performed in a different order than as disclosed below.

Referring to a method 1200 outlined in FIG. 12, step 1210 can involve delivering a clot retrieval device across a target clot. The clot retrieval device can be delivered through a microcatheter or other suitable delivery catheter and have a collapsed configuration during delivery and an expanded deployed configuration when the delivery catheter is retracted. An elongate shaft can be used to manipulate the device by a user. An expandable element can be attached to the distal end of the elongate shaft and have an outer body extending along a longitudinal axis with a substantially tubular lumen. An inner body can be disposed along the axis within the lumen of an outer body and be radially expandable to a lesser extent than the outer body such that it is fully contained. The inner body and outer body can be capable of translation along and/or about the longitudinal axis relative to each other such that the device transitions from the deployed configuration to pinch and grip a clot in a clot pinching configuration.

In many cases, the inner body may expand to only a slightly smaller overall diameter than the outer body and be configured to develop a radial force that can be greater than, less than, or equal to that developed by the outer body. This allows the inner and outer bodies to be tailored for the size, location, and composition of a target clot so as to increase the probability of first pass success for the device.

The inner body and outer body can both be made from struts forming a plurality of cells. The cells can be any of a variety of shapes and sizes. In step 1220, the bodies can be configured so that when expanded and deployed, the openings in the cells of both bodies are largely aligned in both the axial and circumferential directions. The cells can have large central openings so that when expanded, the device can appose the vessel walls while the limited scaffolding provided by the struts compresses and imbeds with the target clot. Portions of the clot in the vicinity can then easily pass inward simultaneously through gaps in the inner and outer body cells.

The devices can be configured so that the elongate shaft is made up of a first shaft connected to the proximal end of the outer body and a second shaft connected to the proximal end of the inner body, as in step 1230. The second shaft can, for example, be coincident with the first shaft so that it can selectively be used to linearly translate or rotate the inner body independent of the outer body. Similarly, the first shaft can be used to linearly translate or rotate the outer body independent of the inner body.

Alternately, some other mechanism can be utilized in this step to pinch the clot. The proximal support arms of the inner or outer body, for example, can be formed at an angle to the longitudinal axis, such that a twist can be imparted on one of the bodies relative the other if a microcatheter or outer catheter is advanced to the support arms beyond the proximal end of the expandable bodies.

The device can be delivered in the collapsed delivery configuration to the occluded vessel through a microcatheter. In the case of an intracranial occlusion a variety of access routes are possible, including a direct stick into the carotid artery, a brachial approach, or a femoral access. Once access has been gained to the arterial system using conventional and well understood techniques, a guide catheter or long sheath is typically placed as close to the occlusive clot as practical. For example, in the case of a middle cerebral artery occlusion, the guide catheter might be placed in the internal carotid artery proximal of the carotid siphon. A microcatheter can then be advanced across a clot with or without the aid of a guidewire. Once the microcatheter tip has been advanced across and distal of the clot the guidewire, if used, can be removed and the clot retrieval device is advanced through the microcatheter until it reaches the distal end. The microcatheter can then retracted which allows the clot retrieval device to expand within and to either side of the occlusive clot.

Step 1240 involves deploying the clot retrieval device to the expanded deployed configuration. The radial force applied by the inner and outer bodies of the device can urge at least a portion of the clot radially inwards through the aligned cell openings. Clot compression can be controlled and minimized because the applied radial force does not need to be very high, since it is not necessary for large portions of the clot to fully enter the inner lumen of the device. Minimizing compression of the clot reduces the frictional forces to be overcome when dislodging and retracting the clot.

Continuing to FIG. 13, method 1300 can have a step 1310 translating the inner body relative to the outer body or the outer body relative to the inner body to pinch in compression at least a portion of the clot between the struts of the inner body cells and outer body cells. The translation can be linear motion, a rotation, or a combination of the two. Enacting the translation can be accomplished through a system with an inner and outer shaft as described earlier. Alternately, advancing an outer catheter over a proximal portion of the device disposed as a spiral can impose tangential forces on the spiral portion of the device to twist and or rotate relative to other portions. Regardless, a relative translation serves to pinch the clot in compression between the struts of the cells of the inner body and the struts of the cells of the outer body. This step can be done with the aid of aspiration through the outer and/or guide catheter to assist in retaining a firm grip on the clot and avoiding fragment loss. Should it be necessary during a procedure, reversing the process of step 1310 can transition the device from the clot pinching configuration back to the expanded deployed configuration.

If a microcatheter or other outer catheter is advanced to increase the pinch on a clot, the user may feel the pinching as resistance and stop advancement of the catheter, or alternately may advance a fixed distance over the proximal end of the expandable bodies. The relatively low level of scaffolding in the expandable bodies allows the relative tension between the device and catheter to be maintained so that the pinch does not deteriorate during retraction of the clot.

In step 1320, the inner or outer shaft can be provided with features, such as a pin in a slot or a cam and follower arrangement, to limit the total relative motion between the inner and outer bodies when transitioning to and from the clot pinching configuration. Limiting the translation ensures that the clot is pinched but not sheared or fragmented.

In step 1330 the clot retrieval device with the pinched clot can be withdrawn from the vessel while maintaining the pinch between the cells of the inner body and outer body. Along with aspiration, this engagement maintains the firm pinching grip on the clot as it is withdrawn through bends and successively larger vessel diameters.

In step 1340, the clot retrieval device and the pinched clot can be removed from the patient. If required, the device may be rinsed in saline and gently cleaned before being reloaded into the microcatheter. It can then be reintroduced into the vasculature to be redeployed in additional segments of occlusive clot, or if further passes for complete recanalization are needed.

The invention is not necessarily limited to the examples described, which can be varied in construction and detail. The terms "distal" and "proximal" are used throughout the preceding description and are meant to refer to a positions and directions relative to a treating physician. As such, "distal" or distally" refer to a position distant to or a direction away from the physician. Similarly, "proximal" or "proximally" refer to a position near to or a direction towards the physician. Furthermore, the singular forms "a," "an," and "the" include plural referents unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

In describing example embodiments, terminology has been resorted to for the sake of clarity. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology. For clarity and conciseness, not all possible combinations have been listed, and such variants are often apparent to those of skill in the art and are intended to be within the scope of the claims which follow.

What is claimed is:

1. A device for removing a clot from a blood vessel having a constrained delivery configuration and an expanded deployed configuration, the device comprising:
   a first shaft, a second shaft, and a framework of struts forming an expandable member extending distally from the first and second shafts, the expandable member comprising:
      an inner tubular lumen and a longitudinal axis extending therethrough;
      an inner body connected to the second shaft comprising a plurality of cells expandable in the deployed configuration around the longitudinal axis; and
      an outer body connected to the first shaft comprising a plurality of cells expandable in the deployed configuration to a greater extent than the inner body, the outer body disposed around the inner body;
   wherein the first shaft is coincident with the second shaft and the longitudinal axis;
   wherein the inner body and outer body are independently translatable and rotatable with respect to each other about the longitudinal axis between the deployed configuration and a clot pinching configuration;
   wherein the cells of the inner body and the cells of the outer body are configured to pinch a clot located in the cells when in the clot pinching configuration;
   wherein the plurality of cells of the inner body are aligned with the plurality of cells of the outer body in the expanded deployed configuration;
   wherein the plurality of cells of the inner body are not aligned with the plurality of cells of the outer body in the clot pinching configuration and; wherein the clot pinching configuration is achieved by distally translating the inner body relative to the outer body until at least a portion of the clot is compressed between the plurality of cells of the inner body and the plurality of cells of the outer body.

2. The device of claim 1, wherein the plurality of cells of the inner body are approximately equal in size to the plurality of cells of the outer body.

3. The device of claim 1, wherein the plurality of cells of the inner and outer bodies are configured to embed in the clot in the expanded deployed configuration.

4. The device of claim 1, wherein the first shaft comprises an elongate body, an internal lumen, and a slot approximate its distal end.

5. The device of claim 4, wherein the second shaft is disposed within the lumen of the first shaft and comprises an indexing pin extending radially from the outer surface of the second shaft, the indexing pin configured to engage with the slot of the first shaft.

6. The device of claim 5, wherein an axis of the slot forms an angle with the longitudinal axis such that linear translation of the second shaft with respect to the first shaft causes rotation of the indexing pin within the slot.

7. The device of claim 1, wherein regions of the inner body and outer body are configured to exert an outward radial force on the clot to urge the clot towards the inner tubular lumen.

8. A device for treating an occlusion in a body vessel, the device comprising:
a tubular inner lumen configured about a longitudinal axis;
an inner body comprising a constrained delivery configuration, an expanded deployed configuration, and a plurality of struts forming an inner clot scaffolding section comprising rings of cells;
an outer body disposed around the inner body comprising a constrained delivery configuration, an expanded deployed configuration, and a plurality of struts forming an outer clot scaffolding section comprising rings of cells; and
an elongate shaft assembly extending proximal to the inner and outer bodies, the elongate shaft assembly comprising a first tubular shaft connected to the outer body and a second shaft connected to the inner body,
wherein the first tubular shaft surrounds and is coincident with the second shaft and the longitudinal axis;
wherein the inner body and outer body are independently translatable and rotatable with respect to each other about the longitudinal axis between the deployed configuration and a clot pinching configuration;
wherein at least a portion of a clot is compressed between the struts of the inner body and the struts of the outer body when the inner body is in the clot pinching configuration;
wherein in the expanded deployed configuration, the cells of the inner body are aligned with the cells of the outer body;
wherein the cells of the inner body are not aligned with the cells of the outer body in the clot pinching configuration and; wherein the clot pinching configuration is achieved by distally translating the inner body relative to the outer body until at least a portion of the clot is compressed between the plurality of cells of the inner body and the plurality of cells of the outer body.

9. The device of claim 8, wherein the cells of the inner body are approximately equal in size to the cells of the outer body.

10. The device of claim 8, wherein the scaffolding sections of the inner and outer bodies are configured to exert an outward radial force on a clot to urge the clot radially inwards towards the inner tubular lumen.

11. The device of claim 8, wherein the second shaft is disposed within a lumen of the first tubular shaft and comprises an indexing pin extending radially from the outer surface of the second shaft, the indexing pin configured to engage with a slot of the first tubular shaft.

12. The device of claim 8, wherein the first tubular shaft and the second shaft are configured to translate and rotate the inner body with respect to the outer body.

13. The device of claim 8, wherein the struts of the scaffolding sections of the inner and outer bodies are configured for embedding in a clot in the expanded deployed configuration.

14. A method of treating a patient with a clot occluding a vessel, the method comprising the steps of:
delivering a clot retrieval device across the clot, the clot retrieval device comprising:
a collapsed delivery configuration, an expanded deployed configuration, an elongate shaft assembly, and an expandable element distal of the elongate shaft, the expandable element comprising:
an inner body comprising a plurality of cells;
an outer body extending along a longitudinal axis around the inner body comprising plurality of cells and expandable in the deployed configuration to a greater extent than the inner body, the outer body disposed around the inner body;
the inner body configured to translate distally relative to the outer body about the longitudinal axis between the deployed configuration and a clot pinching configuration;
deploying the clot retrieval device to the expanded deployed configuration so that the cells of the inner and outer bodies are aligned;
exerting a radial force with the device so that at least a portion of the clot is urged radially inwards through the cell openings of the inner and outer bodies;
translating the inner body distally, relative to the outer body to pinch in compression at least a portion of the clot between the struts of the inner and outer body cells such that the plurality of cells of the inner body are not aligned with the plurality of cells of the outer body;
withdrawing the clot retrieval device from the vessel while maintaining at least a portion of the relative translation between the inner body and the outer body to maintain grip on the clot; and
removing the clot retrieval device and the pinched clot from the patient,
wherein the elongate shaft assembly comprises a first tubular shaft connected to the outer body and a second shaft, the second shaft residing within a lumen of the first tubular shaft and connected to the inner body, the first shaft and second shaft configured to be selectively movable with respect to each other; and
wherein the first shaft selectively imparts the motion on the outer body relative to the inner body and the second shaft selectively imparts the motion on the inner body relative to the outer body.

15. The method of claim 14, wherein the first shaft is configured to limit the range of translation of the second shaft.

* * * * *